US011761025B2

(12) United States Patent
Fernando (10) Patent No.: US 11,761,025 B2
(45) Date of Patent: *Sep. 19, 2023

(54) PRESERVATION OF CELL-FREE NUCLEIC ACIDS (71) Applicant: STRECK LLC, La Vista, NE (US)

(72) Inventor: M. Rohan Fernando, Omaha, NE (US)

(73) Assignee: STRECK LLC, La Vista, NE (US)

(*) Notice: Subject to any disclaimer, the term of this patent is extended or adjusted under 35 U.S.C. 154(b) by 231 days.

This patent is subject to a terminal disclaimer.

(21) Appl. No.: 16/908,233

(22) Filed: Jun. 22, 2020

(65) Prior Publication Data

US 2020/0318161 A1 Oct. 8, 2020

Related U.S. Application Data (63) Continuation of application No. 16/377,344, filed on Apr. 8, 2019, now Pat. No. 10,689,686, which is a continuation of application No. 15/937,446, filed on Mar. 27, 2018, now Pat. No. 10,294,513, which is a continuation of application No. 15/894,077, filed on Feb. 12, 2018, now Pat. No. 10,144,955, which is a continuation of application No. 15/601,682, filed on May 22, 2017, now Pat. No. 9,926,590, which is a continuation of application No. 14/071,969, filed on Nov. 5, 2013, now Pat. No. 9,657,227, which is a continuation of application No. 13/648,415, filed on Oct. 10, 2012, now Pat. No. 8,586,306, which is a continuation of application No. 12/704,030, filed on Feb. 11, 2010, now Pat. No. 8,304,187.

(60) Provisional application No. 61/153,472, filed on Feb. 18, 2009.

(51) Int. Cl.
C12Q 1/68 (2018.01)
C12Q 1/6806 (2018.01)
C09K 15/20 (2006.01)

(52) U.S. Cl.
CPC .......... *C12Q 1/6806* (2013.01); *C09K 15/20* (2013.01); *C12Q 2527/125* (2013.01); *C12Q 2527/127* (2013.01)

(58) Field of Classification Search
CPC .............. C12Q 1/6806; C09K 15/20
See application file for complete search history.

(56) References Cited

U.S. PATENT DOCUMENTS

| | | |
|---|---|---|
| 1,432,249 A | 10/1922 | Robert |
| 1,922,799 A | 8/1933 | Gaus |
| 2,250,666 A | 7/1941 | Webb |
| 2,690,624 A | 10/1954 | Phillips |
| 2,930,570 A | 3/1960 | Leedy |
| 3,781,120 A | 12/1973 | Engelhardt |
| 3,867,521 A | 2/1975 | Miskel et al. |
| 3,872,730 A | 3/1975 | Ringrose et al. |
| 3,874,384 A | 4/1975 | Deindoerfer |
| 3,879,295 A | 4/1975 | Glover et al. |
| 3,973,913 A | 8/1976 | Louderback |
| 3,994,085 A | 11/1976 | Groselak et al. |
| 4,043,453 A | 8/1977 | Greenlee |
| 4,318,090 A | 3/1982 | Narlow et al. |
| 4,513,522 A | 4/1985 | Selenke |
| 4,515,890 A | 5/1985 | Manderino et al. |
| 4,579,759 A | 4/1986 | Breuers |
| 4,584,219 A | 4/1986 | Baarttnans |
| 4,675,159 A | 6/1987 | Al-Sioufi |
| 4,884,827 A | 12/1989 | Kelley |
| 4,921,277 A | 5/1990 | McDonough |
| 5,000,484 A | 3/1991 | Phelan et al. |
| 5,060,672 A | 10/1991 | Sandor et al. |
| 5,110,908 A | 5/1992 | Deich et al. |
| 5,135,125 A | 8/1992 | Andel et al. |
| 5,196,182 A | 3/1993 | Ryan |
| 5,213,765 A | 5/1993 | Kasai et al. |
| 5,250,438 A | 10/1993 | Ryan |
| 5,257,633 A | 11/1993 | Vogler et al. |
| 5,260,048 A | 11/1993 | Ryan |
| 5,343,647 A | 9/1994 | Bulka |
| 5,366,249 A | 11/1994 | Diemert |
| 5,447,842 A | 9/1995 | Simons |
| 5,457,024 A | 10/1995 | Goldbard |
| 5,459,073 A | 10/1995 | Ryan |
| 5,459,253 A | 10/1995 | Wolin et al. |
| 5,460,797 A | 10/1995 | Ryan |
| 5,468,022 A | 11/1995 | Linder et al. |

(Continued)

FOREIGN PATENT DOCUMENTS

| | | |
|---|---|---|
| CA | 2406463 | 1/2001 |
| DE | 19928820 | 12/2000 |

(Continued)

OTHER PUBLICATIONS

American Association for Cancer Research; 93rd Annual Meeting; Apr. 6-10, 2002; San Francisco, California; vol. 43, Mar. 2002.
Ashoor, G et al., "Trisomy 13 detection in the first trimester of pregnancy using a chromosome-selective cell-free DNA analysis method" Ultrasound in Obstetrics & Gynecology; 41(1):21-5, Nov. 23, 2012.
Barrett et al., "Implementing Prenatal Diagnosis Based on Cell-Free Fetal DNA: Accurate Identification of Factors Affecting Fetal DNA Yield," PLoS One, 6(10):e25202, Oct. 4, 2011.
Bayindir, B et al., "Noninvasive Prenatal Testing Using a Novel Analysis Pipeline to Screen for All Autosomal Fetal Aneuploidies Improves Pregnancy Management," European Journal of Human Genetics. Jan. 14, 2015.

(Continued)

Primary Examiner — Kenneth R Horlick
(74) Attorney, Agent, or Firm — MARSHALL, GERSTEIN & BORUN LLP (57) ABSTRACT A method for preserving and processing cell-free nucleic acids located within a blood sample is disclosed, wherein a blood sample containing cell-free nucleic acids is treated to reduce both blood cell lysis and nuclease activity within the blood sample. The treatment of the sample aids in increasing the amount of cell-free nucleic acids that can be identified and tested while maintaining the structure and integrity of the nucleic acids.

20 Claims, 2 Drawing Sheets

(56) References Cited

U.S. PATENT DOCUMENTS

| | | |
|---|---|---|
| 5,490,658 A | 2/1996 | Coward et al. |
| 5,501,954 A | 3/1996 | Mahr |
| 5,512,343 A | 4/1996 | Shaw |
| 5,540,358 A | 7/1996 | Wiles et al. |
| 5,560,657 A | 10/1996 | Morgan |
| 5,614,391 A | 3/1997 | Franciskvoich et al. |
| 5,618,664 A | 4/1997 | Kiessling |
| 5,629,147 A | 5/1997 | Asgari |
| D382,343 S | 8/1997 | Wandell et al. |
| 5,654,054 A | 8/1997 | Tropsha |
| 5,688,516 A | 11/1997 | Raad |
| 5,731,156 A | 3/1998 | Golbus |
| 5,783,093 A | 7/1998 | Holme |
| 5,811,099 A | 9/1998 | Ryan |
| 5,817,519 A | 10/1998 | Zelmanovic et al. |
| 5,849,517 A | 12/1998 | Ryan |
| 5,858,699 A | 1/1999 | Granger et al. |
| 5,861,253 A | 1/1999 | Asgari et al. |
| 5,906,744 A | 5/1999 | Carroll et al. |
| 5,962,234 A | 10/1999 | Golbus |
| 5,976,014 A | 11/1999 | Petrick et al. |
| 5,977,153 A | 11/1999 | Camiener |
| 5,985,572 A | 11/1999 | Macfarlane |
| 6,013,240 A | 1/2000 | Behr et al. |
| 6,030,767 A | 2/2000 | Wagner |
| 6,043,032 A | 3/2000 | Yamagishi et al. |
| 6,072,086 A | 6/2000 | James et al. |
| 6,074,827 A | 6/2000 | Nelson |
| 6,077,235 A | 6/2000 | Serpentino et al. |
| 6,125,563 A | 10/2000 | Girerd |
| 6,128,840 A | 10/2000 | Biosvert |
| 6,168,922 B1 | 1/2001 | Harvey et al. |
| 6,177,163 B1 | 1/2001 | Block et al. |
| 6,190,609 B1 | 2/2001 | Chapman |
| 6,197,539 B1 | 3/2001 | Granger |
| 6,197,540 B1 | 3/2001 | Granger |
| 6,210,889 B1 | 4/2001 | Drouin et al. |
| 6,218,531 B1 | 4/2001 | Ekenberg |
| 6,251,638 B1 | 6/2001 | Umansky et al. |
| 6,258,540 B1 | 7/2001 | Lo et al. |
| 6,287,820 B1 | 9/2001 | Umansky et al. |
| 6,337,189 B1 | 1/2002 | Ryan |
| 6,365,362 B1 | 4/2002 | Terstappen et al. |
| 6,527,242 B1 | 3/2003 | Kennedy |
| 6,527,957 B1 | 3/2003 | Deniega |
| 6,551,267 B1 | 4/2003 | Cohen et al. |
| 6,560,847 B2 | 5/2003 | Ohlsson |
| 6,579,672 B1 | 6/2003 | Granger |
| 6,581,973 B2 | 6/2003 | Levine et al. |
| 6,602,718 B1 | 8/2003 | Augello et al. |
| 6,617,170 B2 | 9/2003 | Augello et al. |
| 6,617,180 B1 | 9/2003 | Wang |
| 6,623,983 B1 | 9/2003 | Terstappen et al. |
| 6,630,301 B1 | 10/2003 | Gocke et al. |
| 6,645,731 B2 | 11/2003 | Terstappen et al. |
| 6,664,056 B2 | 12/2003 | Lo et al. |
| 6,759,217 B2 | 7/2004 | Kopreski et al. |
| 6,821,789 B2 | 11/2004 | Augello et al. |
| 6,860,513 B2 | 3/2005 | Kaufman |
| 6,884,573 B2 | 4/2005 | Fischer |
| 6,916,634 B2 | 7/2005 | Kopreski |
| 6,939,671 B2 | 9/2005 | Kopreski |
| 6,994,790 B2 | 2/2006 | Corbin |
| 7,022,478 B2 | 4/2006 | Rainer et al. |
| 7,044,941 B2 | 5/2006 | Mathias |
| 7,208,275 B2 | 4/2007 | Gocke et al. |
| 7,267,980 B1 | 9/2007 | Mortari et al. |
| 7,282,371 B2 | 10/2007 | Helftenbein |
| 7,288,380 B1 | 10/2007 | Gocke et al. |
| 7,318,293 B2 | 1/2008 | Ardern |
| 7,332,277 B2 | 2/2008 | Dhallan |
| 7,332,288 B2 | 2/2008 | Terstappen et al. |
| 7,358,039 B2 | 4/2008 | Fischer |
| 7,390,663 B2 | 6/2008 | Ryan et al. |
| 7,398,999 B2 | 7/2008 | Kaufman |
| 7,419,832 B2 | 9/2008 | Hunsley |
| 7,442,506 B2 | 10/2008 | Dhallan |
| 7,445,901 B2 | 11/2008 | Kudlicki et al. |
| 7,478,513 B2 | 1/2009 | Baldwin |
| 7,569,350 B2 | 8/2009 | Gocke et al. |
| 7,651,838 B2 | 1/2010 | Paterlini-Brechot |
| 7,767,460 B2 | 8/2010 | Hunsley et al. |
| 8,304,187 B2 | 11/2012 | Fernando |
| 8,586,306 B2 | 11/2013 | Fernando |
| 9,040,255 B2 | 5/2015 | Tsinberg |
| 9,120,849 B2 | 9/2015 | Chiklis et al. |
| 9,127,048 B2 | 9/2015 | Chiklis et al. |
| 9,657,227 B2 | 5/2017 | Fernando |
| 10,091,984 B2 | 10/2018 | Fernando |
| 2001/0018192 A1 | 8/2001 | Terstappen et al. |
| 2001/0049895 A1 | 12/2001 | Burke |
| 2001/0051341 A1 | 12/2001 | Lo et al. |
| 2002/0045196 A1 | 4/2002 | Mahoney et al. |
| 2002/0066216 A1 | 6/2002 | DeLaCruz |
| 2002/0086346 A1 | 7/2002 | Ryan |
| 2002/0119503 A1 | 8/2002 | Ryan et al. |
| 2003/0232377 A1 | 12/2003 | Thomas |
| 2004/0014107 A1 | 1/2004 | Garcia-Blanco |
| 2004/0038424 A1 | 2/2004 | Maples |
| 2004/0043505 A1 | 3/2004 | Walenciak |
| 2004/0137417 A1 | 7/2004 | Ryan |
| 2005/0029559 A9 | 2/2005 | Ahn et al. |
| 2005/0049793 A1 | 3/2005 | Paterlini-Brechot |
| 2005/0232377 A1 | 3/2005 | Paterlini-Brechot |
| 2005/0107316 A1 | 5/2005 | Strebhardt et al. |
| 2005/0181353 A1 | 8/2005 | Rao et al. |
| 2005/0181463 A1 | 8/2005 | Rao et al. |
| 2005/0277204 A1 | 12/2005 | Hollis et al. |
| 2006/0008807 A1 | 1/2006 | O'Hara |
| 2006/0105372 A1 | 5/2006 | Bair et al. |
| 2006/0194192 A1 | 8/2006 | Rao et al. |
| 2006/0204989 A1 | 9/2006 | Kopreski |
| 2006/0210429 A1 | 9/2006 | Hunsley et al. |
| 2007/0111233 A1 | 5/2007 | Bianchi et al. |
| 2007/0134658 A1 | 6/2007 | Bohmer |
| 2007/0178478 A1 | 8/2007 | Dhallan |
| 2007/0202525 A1 | 8/2007 | Quake et al. |
| 2007/0243548 A1 | 10/2007 | Bischoff |
| 2007/0243549 A1 | 10/2007 | Bischoff |
| 2007/0251337 A1 | 11/2007 | Reed et al. |
| 2007/0298406 A1 | 12/2007 | Martorell et al. |
| 2008/0020390 A1 | 1/2008 | Mitchell et al. |
| 2008/0057502 A1 | 3/2008 | Kopreski |
| 2008/0081689 A1 | 4/2008 | Seelie et al. |
| 2008/0096217 A1 | 4/2008 | Kopreski |
| 2008/0102470 A1 | 5/2008 | Dawson et al. |
| 2008/0108071 A1 | 5/2008 | Thompson |
| 2008/0119645 A1 | 5/2008 | Griffey et al. |
| 2008/0206866 A1 | 8/2008 | Zieglschmid et al. |
| 2008/0261292 A1 | 10/2008 | Kopreski |
| 2008/0286748 A1 | 11/2008 | Hunsley |
| 2008/0318801 A1 | 12/2008 | Leung et al. |
| 2009/0034446 A1 | 2/2009 | Adams et al. |
| 2009/0081678 A1 | 3/2009 | Ryan et al. |
| 2009/0215036 A1 | 8/2009 | Stropp et al. |
| 2009/0308303 A1 | 12/2009 | Burlando |
| 2010/0167271 A1 | 7/2010 | Ryan |
| 2010/0184069 A1 | 7/2010 | Fernando et al. |
| 2010/0209930 A1 | 8/2010 | Fernando |
| 2010/0216153 A1 | 8/2010 | Lapidus et al. |
| 2010/0317107 A1 | 12/2010 | Ryan |
| 2011/0027771 A1 | 2/2011 | Deng |
| 2011/0053208 A1 | 3/2011 | Reiss |
| 2011/0111410 A1 | 5/2011 | Ryan et al. |
| 2012/0164676 A1 | 6/2012 | Tsinberg |
| 2012/0308990 A1 | 12/2012 | TerMaat |
| 2013/0034860 A1 | 2/2013 | Fernando |
| 2014/0054508 A1 | 2/2014 | Fernando |
| 2014/0080112 A1 | 3/2014 | Ryan |
| 2014/0199681 A1 | 7/2014 | Ryan |
| 2015/0301037 A1 | 10/2015 | Tsinberg et al. |
| 2016/0143268 A1 | 5/2016 | Ryan |

(56) References Cited

U.S. PATENT DOCUMENTS

| | | | |
|---|---|---|---|
| 2016/0174544 | A1 | 6/2016 | Fernando et al. |
| 2017/0260569 | A1 | 9/2017 | Fernando |

FOREIGN PATENT DOCUMENTS

| | | | |
|---|---|---|---|
| EP | 1031626 | A1 | 8/2000 |
| EP | 1207208 | A2 | 5/2002 |
| EP | 1217372 | A1 | 6/2002 |
| EP | 1816461 | A1 | 8/2007 |
| EP | 1889921 | A2 | 2/2008 |
| EP | 1425294 | B1 | 7/2008 |
| EP | 2228453 | A1 | 9/2010 |
| EP | 2216416 | | 11/2010 |
| EP | 2411808 | B1 | 2/2012 |
| EP | 2 626 438 | A1 | 8/2013 |
| EP | 2674502 | A1 | 12/2013 |
| WO | 93/05650 | | 4/1993 |
| WO | 94/02646 | | 2/1994 |
| WO | 95/26417 | A1 | 10/1995 |
| WO | 98/02528 | A1 | 1/1998 |
| WO | 98/02740 | A1 | 1/1998 |
| WO | 98/59042 | A1 | 12/1998 |
| WO | 00/06780 | A1 | 2/2000 |
| WO | 00/75647 | A1 | 12/2000 |
| WO | 00/77235 | | 12/2000 |
| WO | 01/79851 | A1 | 10/2001 |
| WO | 01/98542 | | 12/2001 |
| WO | 02/055985 | | 7/2002 |
| WO | 03/018757 | A2 | 3/2003 |
| WO | 03/019141 | A2 | 6/2003 |
| WO | 03/069344 | | 8/2003 |
| WO | 03/095974 | | 11/2003 |
| WO | 2006/100063 | A2 | 9/2006 |
| WO | 2007/022483 | A2 | 2/2007 |
| WO | 2008/107724 | A2 | 9/2008 |
| WO | 2008/111981 | A1 | 9/2008 |
| WO | 2010/078194 | A1 | 7/2010 |
| WO | 2010/096323 | A1 | 8/2010 |
| WO | 2010/123908 | A1 | 10/2010 |
| WO | 2011/014741 | A1 | 2/2011 |
| WO | 2011/057184 | | 5/2011 |
| WO | 2011/082415 | A2 | 7/2011 |
| WO | 2012/145662 | A1 | 10/2012 |
| WO | 2012/166913 | A1 | 12/2012 |
| WO | 2013/086428 | A1 | 6/2013 |
| WO | 2013/123030 | A3 | 8/2013 |
| WO | 2014/029791 | A1 | 2/2014 |

OTHER PUBLICATIONS

Beck., J et al., Digital Droplet PCR for Rapid Quantification of Donor DNA in the Circulation of Transplant Recipients as a Potential Universal Biomarker of Graft Injury. Clinical chemistry; 59(12):1732-41, Dec. 1, 2013.

Benachi, A et al., Cell-Free DNA Analysis in Maternal Plasma in Cases of Fetal Abnormalities Detected on Ultrasound Examination. Obstetrics & Gvnecology; 125(6):1330-7, Jun. 1, 2015.

Bethel, K et al., "Fluid phase biopsy for detection and characterization of circulating endothelial cells in myocardial infarction," Physical biology; 11(1):016002, Feb. 1, 2014.

Bevilacqua, E et al., "Performance of screening for aneuploidies by cell-free DNA analysis of maternal blood in twin pregnancies," Ultrasoand in Obstetrics & Gynecology; 45(1):61-6, Jan. 1, 2015.

Bianchi et al., "PCR Quantification of Fetal Cells in Maternal Blood in Normal and Aneuploid Pregnancies" Am J. Hum. Genet. 61:822-829, 1997.

Bianchi, "Invited Editorial Fetal DNA in Maternal Plasma: The Plot Thickens and the Placental Barrier Thins," The American Society of Human Genetics, 62:763-764, 1998.

Bianchi, D et al., "Fetal sex chromosome testing by maternal plasma DNA sequencing: clinical laboratory experience and biology," Obstetrics & Gynecology; 125(2):375-82, Feb. 1, 2015.

Bianchi, DW et al., "DNA sequencing versus standard prenatal aneuploidy screening" New England Journal of Medicine;370(9):799-808, Feb. 27, 2014.

Bina-Stein, et al., Aurintricarboxylic Acid Is a Nonspecific Enzyme Inhibitor, Department of Chemistry, Yale University, New Haven, Connecticut. 1975, 12:191-193.

Biocept—Expands Patent Protection for Liquid Biopsy Platform dated Jun. 1, 2015; http://ir.biocept.com/releasedetail.cfm?releaseID=915635.

Biocept (BIOC) Announces Patent for Blood Collection and Transport Tube; StreetInsider.com; http://www.streetinsider.com/corporate+news/biocept+(BIOC)+Announces; Jun. 1, 2015.

Bioreceptor Ferro fluids: Novel Characteristics and their Utility in Medical Applications; P. A. Liberti, J. N. Chiarappa, A. C. Hovespian, C. G. Rao; Supplied by the British Library; 1996 Kluwer Academic Publishers.

Botezatu et al., "Genetic Analysis of DNA Excreted in Urine: A New Approach for Detecting Specific Genomic DNA Sequences from Cells Dying in an Organism" Clinical Chemistry 46:8, 1078-1084 (2000).

Brar, H et al., "The fetal fraction of cell-free DNA in maternal plasma is not affected by a priori risk of fetal trisomy," The Journal of Maternal-Fetal & Neonatal Medicine; 26(2):143-5, Jan. 1, 2013.

Bruno, D et al., Use of copy number deletion polymorphisms to assess DNA chimerism. Clinical chemistry; 60(8):1105-14, Aug. 1, 2014.

Buysse, K et al. "Reliable noninvasive prenatal testing by massively parallel sequencing of circulating cell-free DNA from, maternal plasma processed up to 24h after venipuncture," Clinical biochemistry; 46(18):1783-6, Dec. 31, 2013.

Carlsson, A et al., "Circulating Tumor Microemboli Diagnostics for Patients with Non-Small-Cell Lung Cancer," Journal of Thoracic Oncology 9(8):1111-9, Aug. 1, 2014.

Chan et al., "Hypermethylated RASSFIA in maternal Plasma: A Universal Fetal DNA Marker that Improves the Reliability of Noninvasive Prenatal Diagnosis," Clinical Chemistrv, 2211-2218, 52(12), 2006.

Chinnapapagari et al., "Treatment of Maternal Blood Samples with Formaldehyde does not alter the Proportion of Circulatory Fetal Nucleic Acids (DNA and mRNA) in Maternal Plasma", Technical Briefs. University Women's Hospital/Dept. of Research, Basel, Switzerland, pp. 652-655, Apr. 2005.

Chiu, Rosa et al."Effects of Blood-Processing Protocols on Fetal and Total DNA Quantification in Maternal Plasma," Clinical Chemistry 47:9, 1607-1613, 2001.

Chudziak, J et al., "Clinical evaluation of a novel microfluidic device for epitope-independent enrichment of circulating tumour cells inpatients with small cell lung cancer," The Analyst;l41(2):669-78, Nov. 2015.

Chung et al., "Lack of Dramatic Enrichment of Fetal DNA in Maternal Plasma by Formaldehyde Treatment," Clinical Chemistry, 51, No. 3, 2005.

Chung et al.; "Detrimental Effect of Formaldehyde on Plasma RNA Detection" 51 (6): 10, Jul. 12, 2010.

Clark-Ganheart et al., "Use of Cell-Free DNA in the Investigation of Intrauterine Fetal Demise and Miscarriage," Obstetrics & Gynecology 125(6):1321-9, Jun. 1, 2015.

Clinical Applications of Flow Cytometry: Immunophenotyping of Leukemic Cells; Approved Guideline; Jun. 1998; vol. 18 No. 8; NCCLS.

Comas, C et al., "Initial Experience with Non-Invasive Prenatal Testing of Cell-Free DNA for Major Chromosomal Anomalies in a Clinical Setting," The Journal of Maternal-Fetal & Neonatal Medicine; (0):1-6, Aug. 12, 2014.

Costa et al. "Fetal Expressed Gene Analysis in maternal Blood: A New Tool for Noninvasive Study of the Fetus" Clinical Chemistry, vol. 49, No. 6, pp. 981-983, 2003.

Curnow et al., "Detection of Triploid, Molar, and Vanishing Twin Pregnancies by a Single-Nucleotide Polymorphism-Based Noninvasive Prenatal Test," American Journal of Obstetrics and Gynecology; 212(1):79-e1 Jan. 2015.

(56) References Cited

OTHER PUBLICATIONS

Dash et al. "Using Noninvasive Prenatal Testing for Aneuploidies in a Developing Country: Lessons Learnt" Journal of Fetal Medicine, 1(3):131-5, 2014.
Decision to Refuse a European Patent Application dated May 3, 2007, Application No. 03 256 535.0-2113.
Denis et al. "Efficient Detection of BRAF Mutation in Plasma of Patients after Long-term Storage of Blood in Cell-Free DNA Blood Collection Tubes" Clinical Chemistry, 61(6):886-8, Jun. 1, 2015.
Dhallan et al., "Methods to Increase the Percentage of Free Fetal DNA Recovered from the Maternal Circulation," JAMA vol. 291, No. 9, 1114-1119, Mar. 3, 2004.
Dharajiya et al. "Noninvasive Prenatal Testing Using Cell-Free Fetal DNA in Maternal Plasma" Carrent Protocols in Human Genetics, 8-15, Jan. 20, 2015.
Diamond et al. "Diverse and Targetable Kinase Alterations Drive Histiocytic Neoplasms" Cancer discovery: CD-15, Nov. 15, 2015.
Ding, et al., MS Analysis of Single-Nucleotide Differences in Circulating Nucleic Acids: Application to Noninvasive Prenatal Diagnosis, 101:10762-10767, 2004.
Fairbrother et al. "Clinical experience of noninvasive prenatal testing with cell-free DNA for fetal trisomies 21, 18, and 13, in a general screening population" Prenatal Diagnosis; 33(6):580-3, Jun. 1, 2013.
Fernando et al., "Stabilization of cell-free RNA in blood samples using a new collection device" Clinical Biochemistry, vol. 45, No. 16-17, pp. 1497-1502, dated Nov. 1, 2012.
Fernando et al., "Stabilization of Cell-Free RNA in Plasma for Noninvasive Diagnosis and Prognosis" URL:http://www.streck.com/resources/Cell_Stabilization/02_Paper_Cell-Free_RNA_BCT_Stabilization_of_Cell-Free_RNA_in_Plasma.pdf Retrieved on May 15, 2014.
Futch et al., "Initial clinical laboratory experience in noninvasive prenatal testing for fetal aneuploidy from maternal plasma DNA samples" Prenatal Diagnosis; 33(6):569-74, Jun. 1, 2013.
Gielis, E.M., "Cell-Free DNA: An Upcoming Biomarker in Transplantation," American Journal of Transplantation May 13, 2015.
Gil et al. "Cell-free DNA analysis for trisomy risk assessment in first-trimester twin pregnancies" Fetal Diagnosis and Therapy; 35(3):204-11, Nov. 15, 2013.
Gil et al. "Implementation of maternal blood cell-free DNA testing in earlv screening for aneuploidies" Ultrasound in Obstetrics & Gynecology 42(1):34-40, Jun. 7, 2013.
Gil et al. "UK NHS pilot study on cell-free DNA testing in screening for fetal trisomies: factors affecting uptake" Ultrasound in Obstetrics & Gynecology; 45(1):67-73. Jan. 1, 2015.
Gonzalez, et al., "Application of Fetal DNA Detection in Maternal Plasma: A Prenatal Diagnosis Unit Experience," Journal of Histochemistry & Cytochemistry, 53(3):307-314, 2005.
Grömminger et al. "Fetal aneuploidy detection by cell-free DNA sequencing for multiple pregnancies and quality issues with vanishing twins" Journal of Clinical Medicine; 3(3):679-92, Jun. 25, 2014.
Gross et al. "Rapid changes in circulating tumor cells following anti-angiogenic therapy" Convergent Science Physical Oncology; 1(1):015002, Sep. 15, 2015.
Haaland, Arne. *Molecules and models: the molecular structures of main group element compounds.* Oxford University Press, 2008, (abstract available at http://www.oxfordscholarship.com/view/10.1093/acprof:oso/9780199235353.001.0001/acprof-9780199235353-cbapter-12).
Hidestrand et al. "Influence of temperature during transportation on cell-free DNA analysis" Fetal diagnosis and Therapy; 31(2):122-8, 2012.
Hindson et al. "High-throughput droplet digital PCR system for absolute quantitation of DNA copy number" Analytical Chemistry; 83(22):8604-10, Oct. 28, 2011.
Holford et al. Stability of beta-actin mRNA in plasma, Annals of the New York Academy of Science, Aug. 2008, 108-111, 1137.

Holmberg et al. "Akonni TruTip® and Qiagen® methods for extraction of fetal circulating DNA—evaluation by real-time and digital PCR" PloS One 8(8):e73068, Aug. 2013.
Hooks et al. "Non-invasive risk assessment of fetal sex chromosome aneuploidy through directed analysis and incorporation of fetal fraction" Prenatal Diagnosis; 34(5):496-9, May 2014.
http://ir.biocept.com/secfiling.cfm?filingid=1193125-15-16425&cik=1044378; Biocept Completing the Answer; Jan. 21, 2015.
Hynek et al., "MoM-based Approach to Noninvasive Prenatal Testing Using Exponentially Weighted Moving Average Chart and Chromosomal Fingerprint" International Journal of Biomedicine and Healthcare: 12, 2015.
Ignatiadis et al., "Circulating Tumor Cells and Circulating Tumor DNA Challenges and Opportunities on the Path to Clinical Utility" Clinical Cancer Research; 21 (21): 4786-800, Nov. 2015.
Jensen et al. "High-throughput massively parallel sequencing for fetal aneuploidy detection from maternal plasma" PloS One: 8(3): e57381, Mar. 2013.
Jeon et al. "The feasibility study of non-invasive fetal trisomy 18 and 21 detection with semiconductor sequencing platform" PLoS One 9(10):e110240, Oct. 20, 2014.
Juneau et al. "Microarray-based cell-free DNA analysis improves noninvasive prenatal testing" Fetal Diagnosis and Therapy; 36(4):282-6, 2014.
Kadam et al., "Quantitative measurement of cell-free plasma DNA and applications for detecting tumor genetic variation and promoter methylation in a clinical setting" The Journal of Molecular Diagnostics. Jul. 31, 2012;14(4):346-56.
Kagan et al "A Sample Preparation and Analysis System for Indentification of Circulating Tumor Cells"; vol. 25, No. 1; Spring 2002; Journal of Clinical Ligand Assay.
Kashiwasaki et al., "Influence of upper and lower thermoneitral room temperatures (20 °C. and 25 °C.) on fasting and post-prandial resting metabolism under different outdoor temperatures," European Journal of Clinical Nutrition, vol. 44, pp. 405-413, 1990.
Katz et al. No Date. "Mass-Volume Equivalents of Common Chemical Solids," Available at <http://www.chymist.com/Mass-volume%20equivalents.pdf>. Accessed Oct. 22, 2015. 4 pages.
Kelly, Brian N., "Circulating microRNA as a biomarker of human growth hormone administration to patients," Mar. 12, 2013, vol. 6, Issue 3.
Kidess et al. "Mutation profiling of tumor DNA from plasma and tumor tissue of colorectal cancer patients with a novel, high-sensitivity multiplexed mutation detection platform" Oncotarget. Feb. 2015; 6(4):2549.
Kirkizlar et al. "Detection of Clonal and Subclonal Copy-Number Variants in Cell-Free DNA from Patients with Breast Cancer Using a Massively Multiplexed PCR Methodology" Translational oncology. Oct. 31, 2015;8(5):407-16.
Kreuzer et al. "Highly Sensitive and specific Fluorescence Reverse Transcription-PCR Assay for the Psuedogene-free Detection of β-actin Transcripts as Quantitative Reference" Clinical Chemistry, vol. 45, No. 2, pp. 297-300, 1999.
Kwee et al. "Measurement of Circulating Cell-Free DNA in Relation to 18F-Fluorocholine PET/CT Imaging in Chemotherapy-Treated Advanced Prostate Cancer" Clinical and Translational Science. Feb. 1, 2012;5(1):65-70.
Lambert-Messerlian et al. "Feasibility of using plasma rather than serum in first and second trimester multiple marker Down's syndrome screening. Journal of medical screening" Dec. 1, 2012:19(4):164-70.
Lanman et al.. "Analytical and clinical validation of a digital sequencing panel for quantitative, highly accurate evaluation of cell-free circulating tumor DNA" PloS one. Oct. 16, 2015;10(10):e0140712.
Lee et al. "Performance of Momguard, a new non-invasive prenatal testing protocol developed in Korea" Obstetrics & Gynecology Science, Sep. 1, 2015,58(5):340-5.
Lee et al., "Survival of Donor Leukocyte Subpopulations in Immunocompetent Transfusion Recipients: Frequent Long-Term Microchimerism in Severe Trauma Patients," Blood, 3127-3139, 93, 1999.

(56) References Cited

OTHER PUBLICATIONS

Lee, Thomas "Down Syndrome and Cell-Free Fetal DNA in Archived Maternal Serum" (AM J. Obstet Gynecol 2002; 187: 1217-21).
Li, et al., "Detection of Paternally Inherited Fetal Point Mutations for β-Thalassemia Using Size-Fractionated Cell-Free DNA in Maternal Plasma," available at: www.jama.com, 293:843-849, 2005.
Liao et al. "Noninvasive prenatal diagnosis of common aneuploidies by semiconductor sequencing" Proceedings of the National Academy of Sciences. May 20, 2014;111(20):7415-20.
Liu et al. "Placental mosaicism for Trisomy 13: a challenge in providing the cell-free fetal DNA testing" Journal of assisted reproduction and genetics, May 1, 2014;31(5):589-94.
Lo et al. "Fetal Cell-Free Plasma DNA Concentrations in Maternal Blood are Stable 24 hours after" Clinical-Chemistry (Jan. 19, 2012).
Lo et al. "Presence of Fetal DNA in Maternal Plasma and Serum" The Lancet, 350, 485-87, 1997.
Lo et al., "Noninvasive prenatal diagnosis for fetal chromosomal aneuploidies by maternal plasma nucleic acid analysis" Clinical Chemistry, American Association for Clinical Chemistry, Washington DC Lnkd-Doi:10.1373/Clinchem.2007.100016, vol. 54, No. 3, pp. 461-466, Jan. 17, 2008.
Lo, "Fetal DNA in Maternal Plasma: Biology and Diagnostic Applications," Clinical Chemistry 46:12 1903-1906, 2000.
Lo, et al., "Increased Fetal DNA Concentrations in the Plasma of Pregnant Women Carrying Fetuses with Trisomy 21" Clinical Chemistry 45:10, 1747-1751 (1999).
Lo, et al., "Quantitative Analysis of Fetal DNA in Maternal Plasma and Serum: Implications for Noninvasive Prenatal Diagnosis," by The American Society of Human Genetics, 62:768-775, 1998.
Lo, Y M Dennis "Circulating Nucleic Acids in Plasma and Serum: An Overview", Annals of the New York Academy of Sciences vol. 945, Issue pp. 1-291 (Sep. 2001).
Lo, Y M Dennis "Molecular Testing of Urine: Catching DNA on the way out" Clinical Chemistry 46, No. 8, 2000.
Lo, Y M Dennis, "Fetal Nucleic Acids in Maternal Plasma, Toward the Development of Noninvasive Prenatal Diagnosis of Fetal Chromosomal Aneuploidies," New York Academy of Sciences, 2008.
Lu et al. Detection and Characterization of Circulating Tumour Cells from Frozen Peripheral Blood Mononuclear Cells, Journal of Circulating Biomarkers. Dec. 1, 2015;35(12):1243-6.
Machaca et al. "Characterization of apoptosis-like endonuclease activity in avian thymocytes," Biology of the Cell, 15-22, 76(1), Elsevier, Paris France, Jan. 1, 1992.
Madabusi et al., "RNA extraction for Arrays," Methods in Enzymology, 1-14, 411, 2006.
McCullough et al. "Non-invasive prenatal chromosomal aneuploidy testing-clinical experience: 100,000 clinical samples" PLoS One. Oct. 7, 2014,9(10):e109173.
Nair et al. "An observational study of circulating tumor cells and (18) F-FDG PET uptake in patients with treatment-naive non-small cell lung cancer" PloS One. Jul. 5, 2013;8(7):e67733.
Nicolaides et al. "Validation of targeted sequencing of single-nucleotide polymorphisms for non-invasive prenatal detection of aneuploidy of chromosomes 13, 18, 21, X, and Y" Prenatal Diagnosis. Jun. 1, 2013;33(6):575-9.
Norton et al. "Cell-free DNA analysis for noninvasive examination of trisomy" New England Journal of Medicine. Apr. 23, 2015;372(17):1589-97.
Norton et al. "Non-invasive Chromosomal Evaluation (NICE) Study: results of a multicenter prospective cohort study for detection of fetal trisomy 21 and trisomy 18" American Journal of Obstetrics and Gynecology, Aug. 31, 2012;207(2):137-e1.
Ono et al. "Circulating microRNA Biomarkers as Liquid Biopsy for Cancer Patients: Pros and Cons of Current Assays" Journal of clinical medicine. Oct. 23, 2015;4(10):1890-907.
Palmer et al., "Flow cytometric determination of residual white blood cell levels in preserved samples from leukoreduced blood products," Transfusion, 118-128, 48(1), Jan. 2008.
Pan, et al., "Cell-free Fetal DNA Levels in Pregnancies Conceived by IVF", Human Reproduction, 20(11):3152-3156, 2005.
Persico et al. "Cell-free DNA testing in the maternal blood in high-risk pregnancies after first trimester combined screening" Prenatal Diagnosis. Jan. 1, 2016.
Pertl, et al., "Fetal DNA in Maternal Plasma: Emerging Clinical Applications," by The American College of Obstetricians and Gynecologists, 98:483-490, 2001.
Pinzani et al., "Circulating Nucleic Acids in Cancer and Pregnancy," Methods: A Companion to Methods in Enzymology, 302-307, 40 (4), Academic Press Inc., New York, Apr. 1, 2010.
Punnoose et al. "PTEN loss in circulating tumour cells correlates with PTEN loss in fresh tumour tissue from castration-resistant prostate cancer patients" British Journal of Cancer. Oct. 20, 2015;113(8):1225-33.
Puren et al., Laboratory operations, specimen processing, and handling for viral load testing and surveillance, Journal of Infectious Diseases, S27-S36, 201(supp 1), University of Chicago Press, Chicago 11, Apr. 15, 2010.
Quezada et al. "Fetal fraction of cell-free DNA in maternal plasma in the prediction of spontaneous preterm delivery," Ultrasound in Obstetrics & Gynecology. Jan. 1, 2015;45(1):101-5.
Quezada et al. "Screening for trisomies 21, 18 and 13 by cell-free DNA analysis of maternal blood at 10-11 weeks' gestation and the combined test at 11-13 weeks" Ultrasound in Obstetrics & Gynecology. Jan. 1, 2015;45(1):36-41.
Rait et al. "Conversions of fotmaldehyde-modified 2'-deoxy adenosine 5'-monophosphate in conditions modeling formalin-fixed tissue dehydration" J. Histochem Cytochem 54(3): 301-10 (Mar. 1, 2006).
Risberg B. "Establishment of PCR based methods for detection of ctDNA in blood." Thesis submitted for the Master's degree in Biomedicine, Oslo University Hospital, Institute for Cancer Research, Department of Genetics and Oslo and Akershus University College of Applied Sciences. May 5, 2013.
Ruiz et al. "Limited genomic heterogeneity of circulating melanoma cells in advanced stage patients" Physical Biology. Feb. 1, 2015;12(1):016008.
Salvianti et al. "Single circulating tumor cell sequencing as an advanced tool in cancer management" Expert review of molecular diagnostics. Nov. 27, 2015:1-3.
Samango-Sprouse et al., "SNP-based non-invasive prenatal testing detects sex chromosome aneuploidies with high accuracy" Prenatal diagnosis. Jul. 1, 2013;33(7):643-9.
Samoila et al., "Method development and validation for clinical cfDNA extraction from blood" InASCO Annual Meeting Proceedings May 20, 2015 (vol. 33, No. 15_suppl, p. e22185).
Samuel et al. "The effect of chorionic villus sampling on the fraction of cell-free fetal DNA in maternal plasma" The Journal of Maternal-Fetal & Neonatal Medicine. Oct. 15, 2015:1-4.
Schatz et al.; "Preservation of Cell-Free DNA in Stored Blood Samples for the Analysis of the (M) Sept9 Colorectal Cancer Screening Marker Enables Sample Shipment'by Mail", May 2011, Published as a poser at the conference on International federation of clinical chemistry and laboratory medicine Worldlab and EU, Berlin, Germany.
Scheffer et al. "Noninvasive fetal blood group genotyping of rhesus D, c, E and of K in alloimmanised pregnant women: evaluation of a 7-year clinical experience" BJOG: An International Journal of Obstetrics & Gynaecology. Oct. 1, 2011:118(11):1340-8.
Schiavon et al. "Analysis of ESR1 mutation in circulating tumor DNA demonstrates evolution during therapy for metastatic breast cancer" Science translational medicine. Nov. 17, 2015;(313):313ra182-.
Sekizawa et al.; "Apoptosis in Fetal Nucleated Erythrocytes Circulating in Maternal Blood" Prenatal Diagnosis; 20: 886-889, 2000.
Seo et al. "An Experience of Using the Harmony Test for Genomics-Based Non-Invasive Prenatal Testing" Journal of Laboratory Medicine and Quality Assurance. Mar. 1, 2015,37(1):44-6.
Shi et al. "Feasibility of noninvasive prenatal testing for common fetal aneuploidies in an early gestational window" Clinica Chimica Acta. Jan. 15, 2015;439:24-8.
Sigma-Aldrich. "1-Aza-3,7-dioxabicyclo[3.3.0]octane-5-methanol solution." Available online at www.sigmaaldrich.com/catalog/product/aldrich/417807?lang=en&region=US. 5 pages. Accessed Jan. 13, 2014.

(56) References Cited

OTHER PUBLICATIONS

Sillence et al. "Fetal Sex and RHD Genotyping with Digital PCR Demonstrates Greater Sensitivity than Real-time PCR" Clinical Chemistry, Nov. 1, 2015;61(11):1399-407.
Smid et al., "Evaluation of Different Approaches for Fetal DNA Analysis from Maternal Plasma and Nucleated Blood Cells", Technical Briefs, pp. 1570-1572, 1999.
Smid et al., "Quantitative Analysis of Fetal DNA in Maternal Plasma in Pathological Conditions Associated with Placental Abnormalities," Annals New York Academy of Sciences, 951:133-137, 2001.
Song et al. "Non-invasive prenatal testing for fetal aneuploidies in the first trimester of pregnancy" Ultrasound in Obstetrics & Gynecology. Jan. 1, 2015;45(1):55-60.
Sparks et al. "Noninvasive prenatal detection and selective analysis of cell-free DNA obtained from maternal blood: evaluation, for trisomy 21 and trisomy 18" American Journal of Obstetrics and Gynecology; Apr. 30, 2012;206(4):319-e1.
Sparks et al. "Selective analysis of cell-free DNA in maternal blood for evaluation of fetal trisomy" Prenatal Diagnosis. Jan. 1, 2012;32(1):3-9.
Stokowski et al. "Clinical performance of non-invasive prenatal testing (NIPT) using targeted cell-free DNA analysis in maternal plasma with microarrays or next generation sequencing (NGS) is consistent across multiple controlled clinical studies" Prenatal Diagnosis. Dec. 1, 2015;35(12):1243-6.
Stumm et al. "Diagnostic accuracy of random massively parallel sequencing for non-invasive prenatal detection of common autosomal aneuploidies: a collaborative study in Europe" Prenatal Diagnosis. Feb. 1, 2014;34(2):185-91.
Takabayashi et al., "Development of Non-invasive Fetal DNA Diagnosis from Maternal Blood," Prenatal Diagnosis, 15:74-77, 1995.
Thung et al. "Implementation of whole genome massively parallel sequencing for noninvasive prenatal testing in laboratories" Expert Review of Molecular Diagnostics. Jan. 2, 2015;15(1):111-24.
Toro et al., "Comparison of cell stabilizing blood collection tubes for circulating plasma tumor DNA" Clinical Biochemistry. Oct. 31, 2015;48(15):993-8.
Toro. "Detection of PIK3CA Mutations in Plasma Tumor DNA Circulating in Peripheral Blood of Breast Cancer Patients" Thesis submitted for the degree of Master of Science in Molecular and Cellular Biology. Johns Hopkins Uniyersity, Baltimore, Maryland. Apr. 2014.
Tynan et al. Application of risk score analysis to low-coverage whole genome sequencing data for the noninvasive detection of trisomy 21, trisomy 18, and trisomy 13, Prenatal diagnosis. Jan. 1, 2015.
US Food and Drug Adminstration, "Draft Guidance for Industry' Pre-Storage Leukocyte Reduction of Whole Blood and Blood Components Intended for Transfusion, Vaccines." Blood & Biologies, available at www.fda.gov/biologicsbloodvaccines/guidance complianceregulatoryinformation/guidances/blood/ucm076769. htm, last accessed Apr. 13, 2011.
Vandenberghe et al. "Non-invasive detection of genomic imbalances in Hodgkin/Reed-Sternberg cells in early and advanced stage Hodgkin's Tymphoma by sequencing of circulating cell-free DNA: a technical proof-of-principle study" The Lancet Haematology. Feb. 28, 2015;2(2):e55-65.
Verweij et al., "European Non-invasive Trisomy Evaluation (EU-NITE) study: a multicenter prospective cohort study for non-invasive fetal trisomy 21 testing" Prenatal Diagnosis. Oct. 1, 2013;33(10):996-1001.
Wagner "Free DNA—new potential analyte in clinical laboratory diagnostics" Biochem Med (Zagreb) 22(1): 24-38 (2012).
Wang D et al. Exploring Glycan Markers for Immunotyping and Precision-Targeting of Breast Circulating Tumor Cells. Archives of medical research. Dec. 1, 2015.
Wang E et al. "Gestational age and maternal weight effects on fetal cell-free DNA in maternal plasma" Prenatal diagnosis. Jul. 1, 2013;33(7):662-6.
Wang P et al. "Sensitive detection of mono-and polyclonal ESRI mutations in primary tumors, metastatic lesions and cell free DNA of breast cancer patients" Clinical Cancer Research. Oct. 2, 20153:clincanres-1534.
Wang Q et al. "Real-time PCR evaluation of cell-free DNA subjected to various storage and shipping conditions" Genetics and Molecular Research. Jan. 1, 2015;14(4):12797-804.
Wang Y et al. "Maternal mosaicism is a significant contributor to discordant sex chromosomal aneuploidies associated with noninvasive prenatal testing" Clinical chemistry. Jan. 1, 2014;60(1):251-9.
Werner et al. "Analytical Validation and Capabilities of the Epic CTC Platform: Enrichment-Free Circulating Tumour Cell Detection and Characterization" Journal of Circulating Biomarkers. 2015 4:3.
Wiebe et al., "Inhibition of Cell Proliferation by Glycerol" Life Sci., 1991, 48(16): 1511-7.
Wienzek-Lischka et al. "Noninvasive fetal genotyping of human platelet antigen-1a using targeted massively parallel sequencing" Transfusion Apr. 1, 2015.
Willems et al. "The first 3,000 non-invasive prenatal tests (NIPT) with the harmony test in Belgium and the Netherlands" Facts, Views & Vision in ObGyn. 2014;6(1):7.
Wong et al. "Optimizing blood collection, transport and storage conditions for cell free DNA increases access to prenatal testing" Clinical Biochemistry. Aug. 31, 2013;46(12):1099-104.
Woolcock et al. "Noninvasive prenatal testing." Australian Family Physician. Jul. 1, 2014;43(7):432.
Zhang, Yi et al., "Effect of Formaldehyde Treatment on the recovery of cell-free fetal DNA from Maternal Plasma at Different Processing Times" Clinic Chimica Acta 397, 60-64, 2008.
Zill et al. "Cell-free DNA next-generation sequencing in pancreatobiliary carcinomas" Cancer discovery. Oct. 1, 2015;5(10):1040-8.
Co-pending U.S. Appl. No. 12/689,370, filed Jan. 19, 2010, published as 2010/0184069 A1 on Jul. 22, 2010.
U.S. Appl. No. 12/704,030, filed Feb. 11, 2010, granted on Nov. 6, 2012 as U.S. Pat. No. 8,304,187.
U.S. Appl. No. 13/648,415, filed. Oct. 10, 2012, granted on Nov. 19, 2013 as U.S. Pat. No. 8,586,306.
U.S. Appl. No. 14/071,969, filed Nov. 5, 2013, granted on May 23, 2017 as U.S. Pat. No. 9,657,227
Co-pending U.S. Appl. No. 15/601,682, filed May 22, 2017, published on Sep. 14, 2017 as 2017/0260569.
Co-pending U.S. Appl. No. 12/941,437, filed Nov. 8, 2010, published as 2011/0111410 on May 12, 2011.
Co-pending U.S. Appl. No. 10/605,669, filed Oct. 16, 2003, published on Jul. 15, 2004 as 2004/0137417.
Co-pending U.S. Appl. No. 12/850,269, filed Aug. 4, 2010, published on Dec. 16, 2010 as 2010/0317107.
Co-pending U.S. Appl. No. 15/010,549, filed Jan. 29, 2016, published on May 26, 2016 as 2016/0143268.
Co-pending U.S. Appl. No. 13/766,207, filed Feb. 13, 2013, published on Mar. 20, 2014 as 2014/0080112.
Co-pending U.S. Appl. No. 14/153,204, filed Jan. 13, 2014, published on Jul. 7, 2014 as 2014/0199681.
Co-pending U.S. Appl. No. 14/907,167, filed Jan. 22, 2016, published on Jun. 23, 2016 as 2016/0174544.
Passage from confidential document, Streck, Inc. Cell-Free DNA BCT 510(k) Premarket Notification, Sep. 19, 2012.
Rykova et al., "Concentrations of Circulating RNA from Healthy Donors and Cancer Patients Estimated by Different Method," Ann. N.Y. Acad. Sci. (2006) vol. 1075, pp. 328-333.
The Scientific Committee on Cosmetic Product and Non-Food Products intended for Consumers "Opinion Concerning the Determination of Certain Formaldehyde Releasers in Cosmetic Products" Dec. 22, 2002, pp. 1-9.
Slocum et al., "Electron-Microscopic Cytochemical Localization of Diamine and polyamine oxidases in Pea and Maize Tissues," Planta vol. 183, pp. 443-450, (1991).
Miller "A Simple Salting Out Procedure for Extracting DNA from Human Nucleated Cells," Nucleic Acids Research vol. 16, p. 1215 (1988).

(56) References Cited

OTHER PUBLICATIONS

Butler "Genetics and Genomics of Core Short Tandem Repeat Loci Used in Human Identity Testing," Journal of Forensic Science, vol. 51, No. 2, pp. 253-265, Mar. 2006.
Brown "Effect of Blood Collection and Processing on Radioimmunoassay Results for Apolipoprotein B in Plasma" Clinical Chemistry, 36/9, 1662-1666, 1990.
Skidmore et al., "Characterization and Use of the Potent Ribonuclease Inhibitor Aurintricarboxylic Acid for the Isolation of RNA from Animal Tissues," Biochem Journal, 263, pp. 73-80 (1989).
May et al. "How Many Species Are There On Earth?," Science vol. 241 p. 1441-1449, 1988.
Modrek "Genome-wide Detection of Alternative Splicing in Expressed Sequences of Human Genes," Nucleic Acid Research, vol. 29, No. 13 pp. 2850-2859, (2001).
Tong YK, Lo YD. Diagnostic developments involving cell-free (circulating) nucleic acids. Clinica Chimica Acta. Jan. 31, 2006;363(1):187-96.
Su YH, Wang M, Aiamkitsumrit B, Brenner DE, Block TM. Detection of a K-Yas mutation in urine of patients with colorectal cancer. Cancer Biomarkers. Jan. 1, 2005;1(2, 3):177-82.
Cannas A, Kalunga G, Green C, Calvo L, Katemangwe P, Reither K, Perkins MD, Maboko L, Hoelscher M, Talbot EA, Mwaba P. Implications of storing urinary DNA from different populations for molecular analyses. PloS one. Sep. 10, 2009;4(9):e6985.
Cherepanova A, Tamkovich S. Pyshnyi D, Kharkova M, Vlassov V, Laktionov P. Immunochemical assay for deoxyribonuclease activity in body fluids. Journal of immunological methods. Aug. 31, 2007;325(1):96-103.
S.H. Zhang et al.: "Genotyping of urinary samples stored with EDTA for forensic applications", Genetics and Molecular Research, vol. 11, No. 3, May 10, 2012, pp. 3007-3012, XP055291026, DOI: 10.4238/2012.
Antje Milde et al.: "Improved DNA typing of human urine by adding EDTA" Int. J Legal Med, Jan. 1, 1999, pp. 209-210, XP055291033.
Nicole T Vu et al.: "Genotyping for DQA1 and PM loci in urine using PCR-based amplification: Effects of sample volume, storage temperature, preservatives, and aging on DNA extraction and typing", Forensic Science International., vol. 102, No. 1, May 1, 1999, pp. 23-34.
Latifa El Bali et al.: "Comparative Study of Seven Commercial Kits for Human DNA Extraction from Urine Samples Suitable for DNA Biomarker-Based Public Health Studies", Journal of Biomolecular Techniques, Dec. 1, 2014.
Dean, (proceeding national Academy of Sciences (2002) vol. 99, pp. 5261-5266).
European Extended Search Report dated Dec. 13, 2017; Application No. 17185367.4.
Communication of a notice of opposition including exhibits. EP Application No. 10000518.0 (Patent No. EP2228453) dated Sep. 12, 2017.
Hallick et al; Use of Aurintricarboxylic Acid as in Inhibitor of Nucleases During Nucleic Acid Isolation; Nucleic Acid Research, (1977) vol. 4, pp. 3055-3064.
Smit et a; Semiautomated DNA Mutation Analysis Using a Robotic Workstation and Molecular Beacons; Clinical Chemistry, 2001, vol. 47, pp. 739-744.
What are the regulatory Definitions for "Ambient", "Room Temperature" and "Cold Chain" (https://www.gmp-compliance.org/gmp-news/bat-are-the-regulatory-definitions-for-ambient-room-temperature-and-cold-chain) Feb.-Mar. 2017.
Wang and Enkel; Lipoprotient Lipase: from gene to obesity; Am J Physiol Endocrinol Met, 2009, vol. 297, pp. E271-E288.
Canadian Office Action, CA Application No. 2,938,275 dated May 13, 2019.
European Office Action, EP Application No. 13166264.5 dated Jan. 9, 2019.
Swarup et al.; Circulating (cell-free) Nucleic Acids—A Promising, Noninvasive Tool for Early Detection of Several Human Diseases; 2007; FEBS Letters 581, pp. 795-799.
Ames et al.; 1975, An Appraisal of the "Vacutainer" System for Blood Collection, Ann. Clin. Biochem, 12: 151-155.
Brief Communication dated Sep. 17, 2019, Application No. 13706856.5.
Brief Communication dated Nov. 5, 2019, Application No. 13706856.5.
Das, Kausik et al., "Carbon-13 nuclear magnetic resonance analysis of formaldehyde free preservatives" Acta Histochemica, 2012.
Norton, Sheila et al., "A new blood collection device minimizes cellular DNA release during sample storage and shipping when compared to a standard device" Journal of Clinical Laboratory Analysis, 2013.
H.K. Taskinen, "Reduced Fertility Among Female Wood Workers Exposed to Formaldehyde", American Journal of Industrial Medicine (1999).
James E. Gibson, "Formaldehyde Toxicity", Chemical Industry Institute of Toxicology Series, (1980).
Reply to Appeal dated Dec. 24, 2019, Application No. 10000518.0.
Grounds of Appeal dated Aug. 12, 2019, Application No. 10000518.0.
Decision Rejecting the Opposition dated Apr. 2, 2019, Application No. 10000518.0.
Statement of Dr. M. Rohan Fernando, dated Apr. 3, 2019.
First Communication dated Jan. 3, 2022, Application No. 20193258.9.
Extended European Search Report dated Dec. 10, 2020, Application No. 20193258.9.

PRESERVATION OF CELL-FREE NUCLEIC ACIDS

CLAIM OF PRIORITY

This application is a continuation of application Ser. No. 16/377,344, filed Apr. 8, 2019 (issued as U.S. Pat. No. 10,689,686) which is a continuation of application Ser. No. 15/937,446 filed on Mar. 27, 2018 (issued as U.S. Pat. No. 10,294,513), which is a continuation of application Ser. No. 15/894,077 filed on Feb. 12, 2018 (issued as U.S. Pat. No. 10,144,955), which is continuation application of application Ser. No. 15/601,682 filed on May 22, 2017 (issued as U.S. Pat. No. 9,926,590), which is a continuation application of application Ser. No. 14/071,969 filed on Nov. 5, 2013 (issued as U.S. Pat. No. 9,657,227), which is continuation application of application Ser. No. 13/648,415 filed on Oct. 10, 2012 (issued as U.S. Pat. No. 8,586,306), which is a continuation application of application Ser. No. 12/704,030 filed on Feb. 11, 2010 (issued as U.S. Pat. No. 8,304,187), which claims the benefit of the filing date of U.S. Provisional Application Ser. No. 61/153,472, filed on Feb. 18, 2009, the entirety of the contents of each application being hereby incorporated by reference for all purposes.

FIELD OF THE INVENTION

This invention relates to the identification and isolation of cell-free nucleic acids in blood samples and more particularly to the preservation of cell-free RNA within a blood sample.

BACKGROUND OF THE INVENTION

It has been recognized that mRNA obtained from plasma of a blood sample can be useful as an indicator of protein expression. Thus, the presence of extra-cellular or cell-free mRNA in blood plasma has triggered a variety of investigations aimed at determining the source and possible diagnostic capabilities of these nucleic acids. Given that the blood of most healthy individuals ordinarily does not contain substantial amounts of cell-free RNA, elevated amounts of cell-free nucleic acids are usually indicative of a health issue (or pregnancy, as fetal cell-free nucleic acids have been identified in maternal blood). Specifically, elevated presence of cell-free mRNA has been found to indicate the existence of various cancers thereby providing support for the belief that these nucleic acids may originate from tumor cells. Consequently, the identification of cell-free RNA within a blood sample could provide insight into the presence and severity of cancer or some other condition (e.g., diabetes, inflammation, arthritis, infection, or the like), and may thus be an early indicator of such condition. The identification of cell-free RNA within a blood sample may also provide guidance for how best to treat a patient depending upon the relative amounts of cell-free nucleic acids identified within the patient's blood sample. Thus it may be useful not only for diagnosis, but also for patient treatment (e.g., by evaluating a change in the RNA condition of a patient as treatment progresses).

RNA is typically subject to ribonuclease (RNase) activity that reduces the amount of recoverable RNA from a blood sample. However, it has been discovered that despite the presence of ample RNase activity in blood plasma, cell-free mRNA is unexpectedly very stable in vivo and avoids any substantial nuclease mediated degradation. However, after a blood sample is acquired from a patient, cell lysis begins and the nucleic acids from within the blood cells are mixed with the cell-free nucleic acids, making it difficult if not impossible to isolate and distinguish the cell-free mRNA. Further, there is concern about the stability of the cell-free nucleic acids and their ability to avoid nuclease-initiated degradation in vitro. Consequently, the disease indication capability of the cell-free nucleic acids may be diminished as their presence is no longer accurately ascertainable. Ideally, prevention of cell lysis and cell-free nucleic acid degradation within the blood sample would allow for the cell-free nucleic acids to be accurately measured and the presence of any disease risk to be detected.

Efforts to further understand the unexpected stability of the cell-free nucleic acids in vivo have led to the belief that these nucleic acids are able to avoid nuclease activity through protection from proteins or by being packaged into apoptotic bodies. In other words, as cells undergo cell death or apoptosis, apoptotic bodies are produced and the cell-free nucleic acids become encased within a membrane of the apoptotic body, thereby reducing the susceptibility of the nucleic acids to nucleases. However, there is concern that after blood draw the nucleic acids somehow become disassociated from the apoptotic bodies and become vulnerable to nucleases. There is a resulting need to process the blood samples containing the cell-free nucleic acids so that the nucleic acids continue to be unaffected by nucleases throughout processing to produce accurate counts of cell-free nucleic acids for diagnosis purposes.

Metabolic inhibitors have been employed previously to inhibit metabolism in cells. For example, glyceraldehyde, sodium fluoride, and ATA, have been used to inhibit glucose metabolism in blood cells. See, e.g., U.S. Pat. Nos. 5,614,391; and 7,390,663 incorporated by reference herein. The use of formaldehyde-donor preservatives for cell or tissue, or RNA preservation has been described in U.S. Pat. Nos. 5,196,182; 5,260,048; 5,459,073; 5,811,099; 5,849,517; and 6,337,189, incorporated by reference herein.

A number of patent documents address processes for the stabilization and/or identification of nucleic acids located within blood plasma and their diagnostic applications. See, generally, U.S. Pat. Nos. 5,614,391; 5,985,572; 6,617,170; 6,630,301; 6,759,217; 6,821,789; 6,916,634; 6,939,671; 6,939,675; 7,208,275; 7,288,380, 7,569,350 and U.S. Patent Publication Nos. 2008/0057502; 2008/0096217; and 2008/0261292 all incorporated by reference herein. Notwithstanding the above, there remains a need for cell-free RNA isolation and preservation methods that preserve cell-free RNA substantially as it exists at the time of a blood draw in an effort to maximize the amount of recovered cell-free nucleic acid from blood plasma and produce reliable isolation and diagnostic results.

The present invention addresses the need for an efficient and consistent method of preserving and testing of a blood sample for elevated levels of cell-free RNA in plasma of the blood sample, which unexpectedly and surprisingly results in short term inhibition of metabolism (i.e., RNA synthesis); long term fixing of blood cells of the blood sample to prevent leaking of cellular RNA into the plasma; fixing the cellular RNA that is within the blood cells to freeze (e.g., immobilize) the protein expression pattern of the blood cells; and stabilizing and protecting the RNA that is in the plasma from nucleases and proteases.

SUMMARY OF THE INVENTION

The present invention contemplates a screening method for the identification of a disease state, comprising the steps of: contacting a drawn blood sample that includes a plurality of blood cells with a plasma RNA (e.g., mRNA) protective agent; isolating cell-free RNA from the blood sample; and analyzing (e.g., by quantity, quality, or both) the isolated RNA for the presence, absence, or severity of a disease state. The protective agent may be present in an amount and for a time sufficient so that the RNA synthesis is inhibited for at least two hours. The protective agent may be present in an amount so that blood cells of the drawn blood sample are fixed to substantially prevent leaking of cellular RNA into the plasma. The protective agent may be present in an amount so that any cellular RNA that is within the blood cells at the time of the blood draw is substantially preserved to immobilize the protein expression pattern of the blood cells so that the protein expression pattern of the cells remains substantially the same as at the time of the blood draw. The protective agent may be present in an amount so that the RNA that is in the plasma is substantially stabilized against degradation mediated by the combined action of nucleases and proteases.

The protective agent may include one or more preservative agents, one or more enzyme inhibitors, one or more metabolic inhibitors, or any combination thereof. The one or more preservative agents may include a formaldehyde releaser such as one selected from the group consisting of: diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo [3.3.0] octane, 5-hydroxymethyl-1-1aza-3,7dioxabicyclo[3.3.0]octane, 5-hydroxypoly[methyleneoxy]methyl-1-1aza-3,7dioxabicyclo[3.3.0]octane, quaternary adamantine and any combination thereof. The one or more enzyme inhibitors may be selected from the group consisting of: diethyl pyrocarbonate, ethanol, aurintricarboxylic acid (ATA), glyceraldehydes, sodium fluoride, ethylenediamine tetraacetic acid (EDTA), formamide, vanadyl-ribonucleoside complexes, macaloid, heparin, hydroxylamine-oxygen-cupric ion, bentonite, ammonium sulfate, dithiothreitol (DTT), beta-mercaptoethanol, cysteine, dithioerythritol, tris (2-carboxyethyl) phosphene hydrochloride, a divalent cation such as $Mg^{+2}$, $Mn^{+2}$, $Zn^{+2}$, $Fe^{+2}$, $Ca^{+2}$, $Cu^{+2}$ and any combination thereof. The one or more metabolic inhibitors may be selected from the group consisting of: glyceraldehyde, dihydroxyacetone phosphate, glyceraldehyde 3-phosphate, 1,3-bisphosphoglycerate, 3-phosphoglycerate, 2-phosphoglycerate, phosphoenolpyruvate, pyruvate and glycerate dihydroxyacetate, sodium fluoride, $K_2C_2O_4$ and any combination thereof.

The concentration of the preservative agent prior to the contacting step may be at least about 50 g/l. The concentration of the preservative agent prior to the contacting step may be less than about 500 g/l. The concentration of the preservative agent prior to the contacting step may be at least about 200 g/l. The concentration of the preservative agent prior to the contacting step may be less than about 300 g/l. The concentration of the preservative agent prior to the contacting step may be a concentration at which crosslinking of nucleic acids and proteins is observed, as indicated by agarose gel electrophoresis.

The isolating step may include isolating the nucleic acid from plasma of the blood sample. Either or both of the isolating and analyzing steps may occur at least 2 hours, 7 days, or even 14 days after the blood sample is drawn. Either or both of the isolating and analyzing steps may occur without freezing the blood sample (e.g. to a temperature colder than about −30° C. (more preferably colder than about −70° C.)). The analyzing step, the isolating step or both may include a step of contacting the nucleic acid with an enzyme, an amplifier or both.

The contacting step may take place in a blood collection tube into which the blood sample is drawn. The contacting step may take place as the blood sample is drawn. The contacting step may be sufficient so that after a period of at least 7 days from the time the blood sample is drawn, the amount of cell-free RNA present in the blood sample is at least about 90%, at least about 95%, or about 100% of the amount of cell-free RNA present in the blood sample at the time the blood sample is drawn. The contacting step may be sufficient so that after a period of at least about 7 days from the time the blood sample is drawn, the concentration of cell-free RNA relative to the total nucleic acid in the blood sample that is present is at least about 10 times, at least about 20 times, or at least about 50 times the amount of cell-free RNA that would be present in the absence of the contacting step.

The protective agent may include a metabolic inhibitor selected from the group consisting of: glyceraldehyde, dihydroxyacetone phosphate, glyceraldehyde 3-phosphate, 1,3-bisphosphoglycerate, 3-phosphoglycerate, 2-phosphoglycerate, phosphoenolpyruvate, pyruvate and glycerate dihydroxyacetate, sodium fluoride, $K_2C_2O_4$ and any combination thereof. The protective agent may include a protease inhibitor selected from the group consisting of: antipain, aprotinin, chymostatin, elastatinal, phenylmethylsulfonyl fluoride (PMSF), APMSF, TLCK, TPCK, leupeptin, soybean trypsin inhibitor, indoleacetic acid (IAA), E-64, pepstatin, VdLPFFVdL, EDTA, 1,10-phenanthroline, phosphoramodon, amastatin, bestatin, diprotin A, diprotin B, alpha-2-macroglobulin, lima bean trypsin inhibitor, pancreatic protease inhibitor, egg white ovostatin egg white cystatin, and any combination thereof. The protective agent may include a phosphatase inhibitor selected from the group consisting of: calyculin A, nodularin, NIPP-1, microcystin LR, tautomycin, okadaic acid, cantharidin, microcystin LR, okadaic acid, fostriecin, tautomycin, cantharidin, endothall, nodularin, cyclosporin A, FK 506/immunophilin complexes, cypermethrin, deltamethrin, fenvalerate, bpV(phen), dephostatin, mpV(pic) DMHV, sodium orthovanadate and any combination thereof.

DETAILED DESCRIPTION

In general, the invention herein contemplates a screening method for the identification of disease presence which includes the preservation and isolation of cell-free nucleic acids located within a blood sample. A unique preservation step acts to increase the amount of recoverable nucleic acids thereby improving the diagnostic capabilities of the cell-free nucleic acids.

The present invention provides a method for the isolation of nucleic acids using a protective agent. The nucleic acid may be DNA, RNA, or any combination thereof. The nucleic acid may be cell-free DNA, cell-free RNA, or any combination thereof. The samples from which the nucleic acids may be isolated include any blood sample. The cell-free nucleic acids may be located within plasma. The method disclosed herein allows for the efficient preservation and isolation of cell-free (e.g., extra-cellular) nucleic acids while avoiding possible mixing with nucleic acids originating within the blood cells that enter a blood sample due to cell lysis after blood draw.

The process for improved cell-free nucleic acid isolation from a blood sample begins by contacting a blood sample with a protective agent containing one or more active ingredients to maintain the integrity of the components within the sample. The one or more active ingredients may include a preservative agent. The preservative agent may include a formaldehyde donor composition. Ingredients that may be used as a preservative agent include, but are not limited to, diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo[3.3.0]octane, 5-hydroxymethyl-1-1aza-3,7dioxabicyclo [3.3.0]octane, 5-hydroxypoly[methyleneoxy]methyl-1-1aza-3,7dioxabicyclo [3.3.0]octane, quaternary adamantine or any combination thereof. The preservative agent may be selected from the group consisting of diazolidinyl urea (DU), imidazolidinyl urea (IDU), and any combination thereof.

The amount of preservative agent used is generally about 50 to about 500 grams per liter. For example, the preservative agent may comprise about 200 to about 300 grams of DU per liter of buffered salt solution.

As used throughout the present teachings, the protective agent composition preferably is substantially non-toxic. For example, the methods herein (and compositions used herein) are free of separately adding and/or handling of any materially significant concentration (e.g., less than about 1% by weight, more preferably less than about 2000 parts per million, more preferably less than about 1000 parts per million, and still more preferably less than about 500 parts per million) of formaldehyde and/or paraformaldehyde prior to any contact with a blood product sample. Further, the protective agent may be substantially free of guanidinium salts, sodium dodecyl sulfate (SDS), or any combination thereof.

The protective agent may further contain one or more nuclease inhibitors (e.g., enzyme inhibitors) in a suitable amount to prevent DNase and/or RNase activity from decreasing the quality and amount (e.g. by at least about 10% by weight, and more preferably at least about 50% by weight) of cell-free nucleic acids recoverable from the blood sample as compared with a sample that does not include a nuclease inhibitor. Nuclease inhibitors that may be used include, but are not limited to diethyl pyrocarbonate, ethanol, aurintricarboxylic acid (ATA), formamide, vanadyl-ribonucleoside complexes, macaloid, ethylenediamine tetraacetic acid (EDTA), proteinase K, heparin, hydroxylamine-oxygen-cupric ion, bentonite, ammonium sulfate, dithiothreitol (DTT), beta-mercaptoethanol, cysteine, dithioerythritol, tris (2-carboxyethyl) phosphene hydrochloride, or a divalent cation such as $Mg^{+2}$, $Mn^{+2}$, $Zn^{+2}$, $Fe^{+2}$, $Ca^{+2}$, $Cu^{+2}$ and any combination thereof. More preferably, the nuclease inhibitors that may be used include aurintricarboxylic acid (ATA), ethylenediamine tetraacetic acid (EDTA), and any combination thereof. Preferred nuclease inhibitors may bind to nucleases (e.g., RNases) so that the nucleases are no longer capable of contacting the cell-free RNA thereby reducing the adverse effects of nucleases on the quantity and quality of the cell-free RNA. The one or more nuclease inhibitors may be present in an amount sufficient to prevent nuclease activity from reducing the amount of recoverable cell-free RNA by more than about 15%.

The protective agent may also include one or more metabolic inhibitors in a suitable amount to reduce cell metabolism within a blood sample. Metabolic inhibitors that may be used include, but are not limited to glyceraldehyde, dihydroxyacetone phosphate, glyceraldehyde 3-phosphate, 1,3-bisphosphoglycerate, 3-phosphoglycerate, 2-phosphoglycerate, phosphoenolpyruvate, pyruvate and glycerate dihydroxyacetate, sodium fluoride, $K_2C_2O_4$ and any combination thereof. More preferably, the one or more metabolic inhibitors used may include sodium fluoride, glyceraldehyde and any combination thereof. Preferred metabolic inhibitors may reduce degradation of cell-free RNA and also reduce cell lysis so that cellular RNA does not become intermixed with any cell-free RNA. This intermixing of cell-free RNA and cellular RNA may reduce the accuracy of any measurement of the amount of cell-free RNA in a blood sample. As an example, in the event that severity of a specified cancer may be measured by the amount of cell-free RNA in a blood sample, any sample that has not been treated to inhibit metabolism may show an unusually high amount of cell-free RNA, even though much of that cell-free RNA originated within one or more blood cells. Thus, the test result may show a false positive of increased cancer severity when in fact the actual amount of true cell-free RNA was low, representing a cancer of reduced severity. The one or more metabolic inhibitors may be present in an amount sufficient to prevent cell metabolism from reducing the accuracy of any cell-free RNA measurement by more than about 15%.

The protective agent may also include one or more protease inhibiting compounds which may limit RNA synthesis. Such protease inhibiting compounds may include but are not limited to antipain, aprotinin, chymostatin, elastatinal, phenylmethylsulfonyl fluoride (PMSF), APMSF, TLCK, TPCK, leupeptin, soybean trypsin inhibitor, indoleacetic acid (IAA), E-64, pepstatin, VdLPFFVdL, EDTA, 1,10-phenanthroline, phosphoramodon, amastatin, bestatin, diprotin A, diprotin B, alpha-2-macroglobulin, lima bean trypsin inhibitor, pancreatic protease inhibitor, egg white ovostatin, egg white cystatin and any combination thereof. Combinations of protease inhibitors, commonly referred to as a "protease inhibition cocktail" by commercial suppliers of such inhibitors, may also be used within the protective agent. Such "cocktails" are generally advantageous in that they provide stability for a range of proteins of interest. Preferred protease inhibitors may include aprotonin, EDTA, EGTA, PMSF, and any combination thereof. The one or more protease inhibiting compounds may be present in an amount sufficient to prevent RNA synthesis from reducing the accuracy of any cell-free RNA measurement by more than about 15%.

The protective agent may further include one or more phosphatase inhibitors including but not limited to calyculin A, nodularin, NIPP-1, microcystin LR, tautomycin, okadaic acid, cantharidin, imidazole, microcystin LR, okadaic acid, fostriecin, tautomycin, cantharidin, endothall, nodularin, cyclosporin A, FK 506/immunophilin complexes, cypermethrin, deltamethrin, fenvalerate, bpV(phen), dephostatin, mpV(pic) DMHV, sodium orthovanadate and combinations thereof. Phosphatase inhibitor cocktails may also be included within the protective agent, as they also provide stability for a wide range of proteins. Preferred phosphatase inhibitors may include cantharidin, sodium orthovanadate, imidazole and any combination thereof. The one or more phosphatase inhibiting compounds may be present in an amount sufficient to prevent a reduction in the accuracy of any cell-free RNA measurement by more than about 15%.

The protective agent may include one or more polyamines in a suitable amount such that they are capable of binding with any nucleic acids thereby preventing degradation of the nucleic acids. The polyamines that may be added include but are not limited to spermine, spermidine, putrescine, cadaverine, and combinations thereof. Preferably, the polyamines used may include spermine and spermidine.

The initial contacting of the blood sample with the protective agent may be for a time sufficient to inhibit cell lysis, nuclease activity, or any combination thereof. Contacting may occur for at least about 10 seconds, at least about 1 minute, or at least about 2 minutes. Contacting can occur for longer periods of time. For example, contacting may be commenced substantially contemporaneously from the time of blood draw (e.g., within less than about 10 minutes of the blood draw) and it may last until nucleic acids are isolated, screened, and/or tested. The contacting step may also be employed to provide a sample with a longer shelf life. Thus, it is possible that a lapse of time of at least about 2 hours, more preferably at least about 6 hours, at least about 24 hours, at least about 7 days or even at least about 14 days can elapse between the time of blood draw (which may be substantially contemporaneous with the contacting step), and the time of any testing or screening of the sample, and or isolation of the nucleic acids.

The protective agent may comprise an active agent in solution. Suitable solvents include water, saline, dimethylsulfoxide, alcohol and any mixture thereof. The protective agent solution may comprise diazolidinyl urea (DU) and/or imidazolidinyl urea (IDU) in a buffered salt solution. The protective agent solution may further comprise EDTA and ATA. The protective agent solution may also include one or more metabolic inhibitors. The protective agent solution may contain only a fixative and may be substantially free of any additional additives.

The amount of any active ingredient within the protective agent may generally be at least about 0.01% by weight. The amount of any active ingredient within the protective agent may generally be less than about 70% by weight. The protective agent may comprise at least about 10% diazolidinyl urea. The protective agent may comprise less than about 40% diazolidinyl urea. The protective agent may further contain at least about 1% of one or more enzyme inhibitors (e.g., nuclease inhibitors) such as EDTA and ATA. The protective agent may contain less than about 30% of one or more enzyme inhibitors. The protective agent may also contain at least about 1% of one or more metabolic inhibitors. The protective agent may contain less than about 20% of one or more metabolic inhibitors.

The amount of preservative agent (e.g., fixative) relative to the amount of any enzyme inhibitors (e.g., EDTA and ATA) is preferably about 1 to about 10 parts (more preferably about 3 to about 6 parts) by weight of fixative to about 2 parts by weight of enzyme inhibitors. The amount of fixative (e.g. the formaldehyde releaser) relative to the amount of any one or more metabolic inhibitors is preferably about 1 to about 10 parts (more preferably about 3 to about 7 parts) by weight of fixative to about 1 part by weight metabolic inhibitors. The amount of protective agent within a tube prior to blood draw may be at least about 200 g/liter. The amount of protective agent within a tube prior to blood draw may be less than about 1000 g/liter.

The combination of one or more preservative agents (e.g. the formaldehyde releasers), one or more enzyme inhibitors, one or more nuclease inhibitors and one or more metabolic inhibitors within the protective agent results in improved ability to maintain the amount and quality of cell-free RNA within a blood sample and is used in a manner and amount so that such results are obtained. These results are believed unexpected and superior to results obtained by the use of only the preservative agent, only the enzyme inhibitor, only the nuclease inhibitor, only the metabolic inhibitor or any combination including two of the preservative agent, the enzyme inhibitor, the nuclease inhibitor, or the metabolic inhibitor. Therefore, it can be appreciated that a synergistic effect occurs when a preservative agent, enzyme inhibitor, nuclease inhibitor, and metabolic inhibitor are combined.

The protective agent can be located within a specialized device, wherein the protective agent is already present in the device prior to addition of the blood sample, such as that disclosed in U.S. Patent Publication No. 2004/0137417, incorporated by reference herein. More preferably, the device is an evacuated collection container, usually a tube. The tube may preferably be made of a transparent material that will also resist adherence of the cells within a given sample. The interior wall of the tube may be coated or otherwise treated to modify its surface characteristics, such as to render it more hydrophobic and/or more hydrophilic, over all or a portion of its surface. The tube may have an interior wall flame sprayed, subjected to corona discharge, plasma treated, coated or otherwise treated. The tube may be treated by contacting an interior wall with a substance so that the nucleic acids of interest will resist adhering to the tube walls. The surface of the tube may be modified to provide a dual functionality that simultaneously provides an appropriate balance of desired hydrophilicity and hydrophobicity, to allow collection of blood, dispersion of the preservatives herein, and resistance of adhesion of nucleic acids to the inner wall of a blood collection tube. Thus it is possible that any coating may be a functionalized polymeric coating that includes a first polymer and one or more second monomeric and/or polymeric functionalities that are different from (e.g., chemically different from) the first polymer. The coating may include one or more co-polymers (e.g., block copolymer, graft copolymer, or otherwise). For example, it may include a copolymer that includes a first hydrophobic polymeric portion, and a second hydrophilic polymeric portion. The coating may be a water based coating. The coating may optionally include an adhesion promoter. The coating may be applied in any suitable manner, it may be sprayed, dipped, swabbed, or otherwise applied onto some or all of the interior of the blood collection tube. The coating may also be applied in the presence of heat. Preferably any coating applied to the inner wall of a blood collection tube will form a sufficiently tenacious bond with the glass (e.g., borosilicate glass) or other material (e.g., polymeric material) of the tube so that it will not erode or otherwise get removed from the inner wall. Examples of suitable polymeric coatings may include silicon containing polymers (e.g., silanes, siloxanes, or otherwise); polyolefins such as polyethylene or polypropylene; polyethylene terephthalate; fluorinated polymers (e.g., polytetrafluoroethylene); polyvinyl chloride, polystyrene or any combination thereof. Examples of teachings that may be employed to coat an interior of a blood collection tube may be found in U.S. Pat. Nos. 6,551,267; 6,077,235; 5,257,633; and 5,213,765; all incorporated by reference.

The composition included in the tube may be present in an amount sufficient to preserve cell morphology and prevent cell degradation while also preventing deleterious DNase and RNase activity within the cell-free nucleic acids. However, the amount may also be sufficiently small so that any consequential dilution of the sample is substantially avoided, and cell-free nucleic acids in the sample are not materially diluted. A blood sample may be fixed simultaneously as it is drawn into the specialized tube. The tube may also be coated over an exterior wall with a protective coating (e.g., a containment barrier that helps control glass shard fragmentation) such as that disclosed in U.S. Pat. No. 7,419,832, incorporated by reference herein.

Additionally, the protective agent may be in a highly viscous or substantially solid state, such that (for example) it can be used effectively as a substantially solid state coating. Examples of such substantially solid state preservatives can be found in commonly owned co-pending U.S. patent application Ser. No. 12/646,204, incorporated by reference herein. Liquid removal techniques can be performed on the protective agent in order to obtain a substantially solid state protective agent. Liquid removal conditions may preferably be such that they result in removal of at least about 50% by weight, more preferably at least about 75% by weight, and still more preferably at least about 85% by weight of the original amount of the dispensed liquid protective agent. Liquid removal conditions may preferably be such that they result in removal of sufficient liquid so that the resulting composition is in the form of a film, gel or other substantially solid or highly viscous layer; for example it may result in a substantially immobile coating (preferably a coating that can be re-dissolved or otherwise dispersed upon contact with a blood product sample). Thus, liquid removal conditions may preferably be such that they result in a material that upon contact with the sample under consideration (e.g., a maternal blood sample) the protective agent will disperse in the sample, and substantially preserve components (e.g., cell-free nucleic acids) in the sample. Liquid removal conditions may preferably be such that they result in a remaining composition that is substantially free of crystallinity; has a viscosity that is sufficiently high that the remaining composition is substantially immobile at ambient temperature (e.g., it does not exhibit any visibly detectable (as seen by the naked eye) flow when held in a storage device at room temperature on an incline of at least about 45° for at least one hour); or both. In this regard as taught in the forgoing application a colorant may also be employed.

As discussed herein, contacting a blood or plasma sample with the protective agent allows the sample to be stored for a period of time prior to isolating and testing the nucleic acids. A blood or plasma sample may be drawn at one location (e.g., a health care facility), contacted with the protective agent, and later transported to a different remote location (e.g., a laboratory, such as one that is separately housed at a distance of at least about 1 km, 2 km, 3 km, or further away from the draw site) for the nucleic acid isolation and testing process. The nucleic acids can be isolated from the blood or plasma sample and tested at the remote location and the resulting diagnostic information may be reported to the site of the original blood draw. The nucleic acid isolation process may be performed at one remote location and the resulting data can be analyzed to identify the presence, absence or relative severity of a disease state at a third location. Alternatively, the results of the cell-free nucleic acid isolation process may be sent back to the site of the initial blood draw and analyzed there. The resulting diagnostic information may then be sent to a third location or back to the remote location or the site of the initial blood draw.

At any time after the initial contact of the blood or plasma sample with the protective agent, the sample can be treated to isolate the cell-free nucleic acids located within the blood. The nucleic acids may be isolated using any isolation method including those methods disclosed in commonly owned U.S. Patent Publication No. 2009/0081678, incorporated by reference herein. The protective agent may aid in maintaining the integrity of blood cell membranes (e.g., the cell membranes remain intact), so that nucleic acids are not released into the sample from blood cells having ruptured cell membranes. Any cell membrane rupture may cause cellular nucleic acids to enter the plasma making isolation of the cell-free nucleic acids (e.g., identifying and separating cell-free nucleic acids from nucleic acids that originated within a blood cell) more difficult. The fixative agent may act to prevent cell lysis so that the blood cells remain intact and substantially all cellular nucleic acids remain intracellular to avoid unwanted contamination of the cell-free nucleic acids.

After the cell-free nucleic acids have been isolated, they can be tested to identify the presence, absence or severity of a disease state including but not limited to a multitude of cancers. The methods herein thus further contemplate a step of nucleic acid testing. Testing of the nucleic acids can be performed using any nucleic acid testing method including, but not limited to polymerase chain reaction (PCR), reverse transcription polymerase chain reaction (RT-PCR), quantitative real time polymerase chain reaction (Q-PCR), gel electrophoresis, capillary electrophoresis, mass spectrometry, fluorescence detection, ultraviolet spectrometry, DNA hybridization, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof.

The present invention includes a method for isolating and testing cell-free RNA from plasma. The method can be performed on a single sample or on multiple samples simultaneously (e.g., in a multi-well plate). The method includes contacting a plasma sample with a protective agent. The protective agent may include one or more active ingredients as previously discussed so that the blood cells remain intact throughout the blood draw and RNA isolation process. The protective agent may further include one or more RNase or enzyme inhibitors and one or more metabolic inhibitors to maintain the structural integrity of the RNA. After contacting the blood sample with the protective agent, the sample may be centrifuged to separate the plasma. The cell pellet may then be discarded. Alternatively, by contacting a blood sample with the protective agent, the blood sample does not necessarily require immediate processing and can be stored for up to about 14 days at room temperature. Thus the inventions herein contemplate one or more steps of storing and/or otherwise waiting a relatively lengthy period from the time of blood draw and/or contacting until the time of screening, testing or other analysis. Once the sample is processed, an appropriate concentration of salt and alcohol may be added to precipitate the RNA containing material. An organic or other compound such as a phenol derivative or the like may then be added to remove any remaining protein contaminants. Any protein contaminants that still remain may be removed by adding additional amounts of an organic or other compound such as a phenol derivative or the like. After centrifugation, ethanol may be added and the sample centrifuged again. Any remaining liquid may be removed from the sample so only the RNA will remain. The finished product of isolated RNA may then be contacted with a buffer.

Incubation may also occur. For example, incubation may occur on ice or at any temperature between −30° C. and 70° C. A sample may be incubated at about −20° C. A sample may also be stored at room temperature and thus substantially free of any freezing upon blood draw.

Preferably, centrifuging occurs at speeds of about 500 to about 15,000 rpm. Centrifuging may occur at about 1,000 to 13,000 rpm. Centrifuging may be performed at a temperature of about 1-20° C. Centrifuging may be performed at a temperature of about 4-9° C.

Example 1

Blood samples from the same donor are drawn into six separate blood collection tubes (tube 1 through tube 6). Tube 1 contains only EDTA. Tube 2 contains DU and EDTA. Tube 3 contains DU, EDTA and ATA. Tube 4 contains DU, EDTA, ATA and glyceraldehyde. Tube 5 contains DU, EDTA, ATA and sodium fluoride. Tube 6 contains DU, EDTA, ATA, glyceraldehyde and sodium fluoride. All tubes are stored at room temperature and 1 ml aliquots of blood are removed from each tube at hours 1.5, 8, 24, 48, 72 and 96. The blood glucose levels of each sample are measured using a YSI blood glucose meter available from YSI Life Sciences (Yellow Springs, Ohio). The blood glucose concentration of those samples from tube 6 maintained relatively consistent glucose levels over the test period, indicating that the combination of EDTA, DU, ATA, glyceraldehyde and sodium fluoride provided reduced levels of cell metabolism. The results of this example are shown in a graphic format at FIG. 1.

Example 2

Four blood samples from the same donor are drawn into four separate blood collection tubes, tube A through tube D. Tube A contains DU, EDTA, ATA, glyceraldehyde and sodium fluoride. Tube B contains DU, EDTA and ATA. Tube C contains DU and EDTA. Tube D contains only EDTA. All tubes are stored at room temperature and 1 ml aliquots of blood are removed from each tube on day 0, day 1, day 2, and day 3 and plasma is separated. All samples are centrifuged at 800 g for 10 minutes at room temperature to separate the plasma. The plasma is then transferred into new tubes and centrifuged at 1500 g for 10 minutes at room temperature. Free circulating RNA is purified using the QIAamp MinElute Virus Spin kit available from Qiagen, Inc. (Valencia, Calif.). RNA is extracted from each plasma sample. The samples are then amplified by Real Time PCR (using TaqMan® RT PCR reagents available from Applied Biosystems, Foster City, Calif.) to identify the 18S rRNA copy number per ml of plasma. Results showed a consistent relative percentage of 18S rRNA copy number per ml of plasma (about 0%) at each measurement, indicating little or no cellular RNA presence as a result of cell lysis or increased cell metabolism in the plasma samples originating in Tube A (containing DU, EDTA, ATA, glyceraldehyde and sodium fluoride). The 18S rRNA copy number per ml of plasma showed elevated levels at every measurement in those samples originating in tubes B, C, and D indicating an increase in the amount of cellular RNA present as a result of cell lysis or increased cell metabolism. The results of this example are shown in a graphic format at FIG. 2.

Example 3

Blood samples from the same donor are drawn into two separate blood collection tubes. The first tube contains DU, EDTA, ATA, glyceraldehyde and sodium fluoride. The second tube contains only EDTA. Both tubes are stored at room temperature and 1 ml aliquots of blood are removed from each tube on day 0, day 1, day 2, day 7, and day 8 and plasma is separated. All samples are centrifuged at 800 g for 10 minutes at room temperature to separate the plasma. The plasma is then transferred into new tubes and centrifuged at 1500 g for 10 minutes at room temperature. Free circulating RNA is purified using the QIAamp MinElute Virus Spin kit available from Qiagen Inc. (Valencia, Calif.). RNA is extracted from each plasma sample. The samples are then amplified by Real Time PCR (using TaqMan® RT PCR reagents available from Applied Biosystems, Foster City, Calif.) to identify fragments of β-globin and RASSF1A genes within the plasma. Results showed a consistent relative percentage of RASSF1A genes per ml of plasma at each measurement, indicating little decrease of RNA presence in the plasma samples originating in the first tube (containing DU, EDTA, ATA, glyceraldehyde and sodium fluoride). The RASSF1A genes per ml of plasma showed decreased levels at every measurement in those samples originating in the tube containing only EDTA indicating a decrease in the amount of cell-free RNA present over time. The results of this example are shown in a graphic format at FIG. 3.

Figure 1:
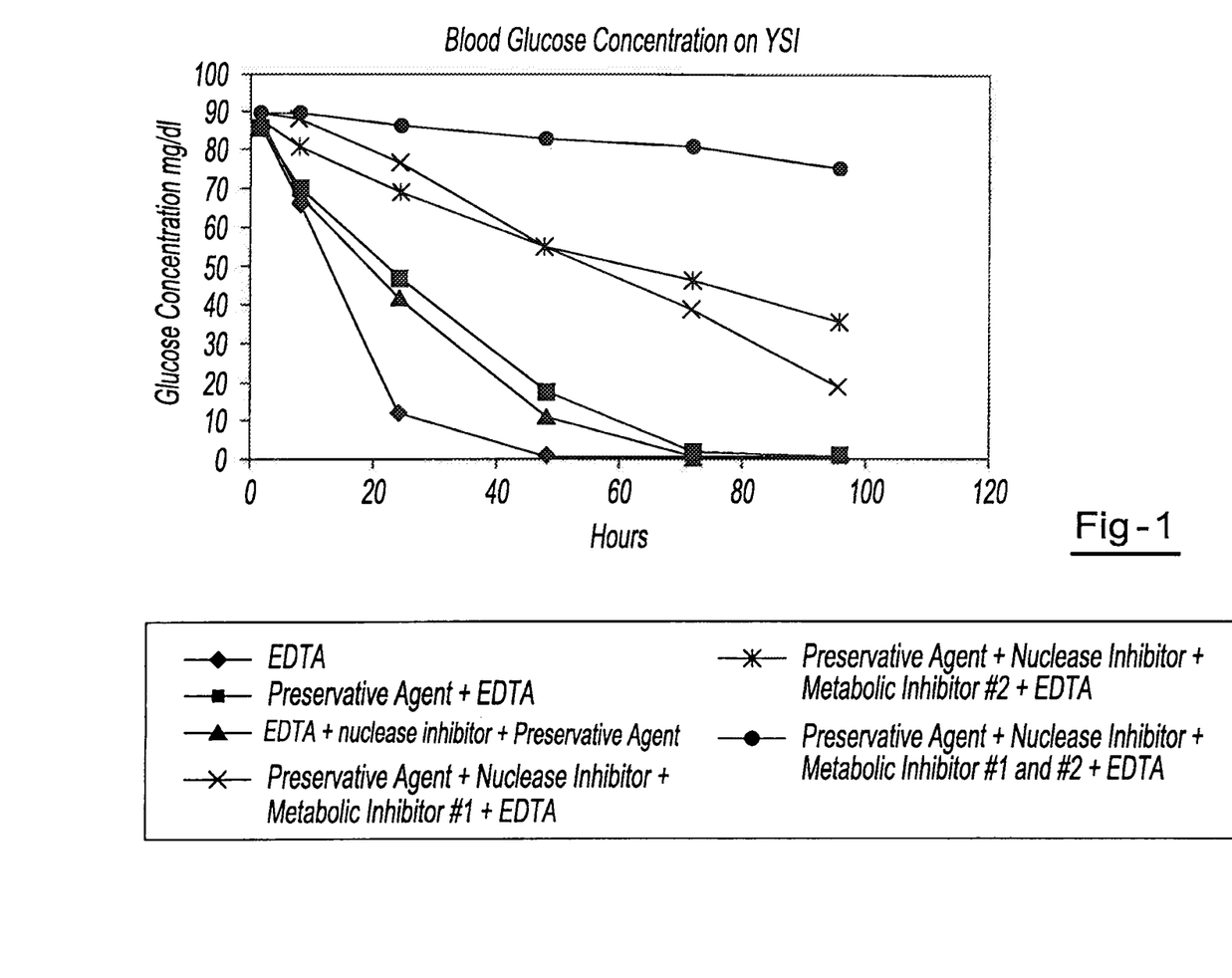
FIG. 1 is a graphic representation showing the glucose concentration present within blood samples contacted with six different compositions over time.
Figure 2:
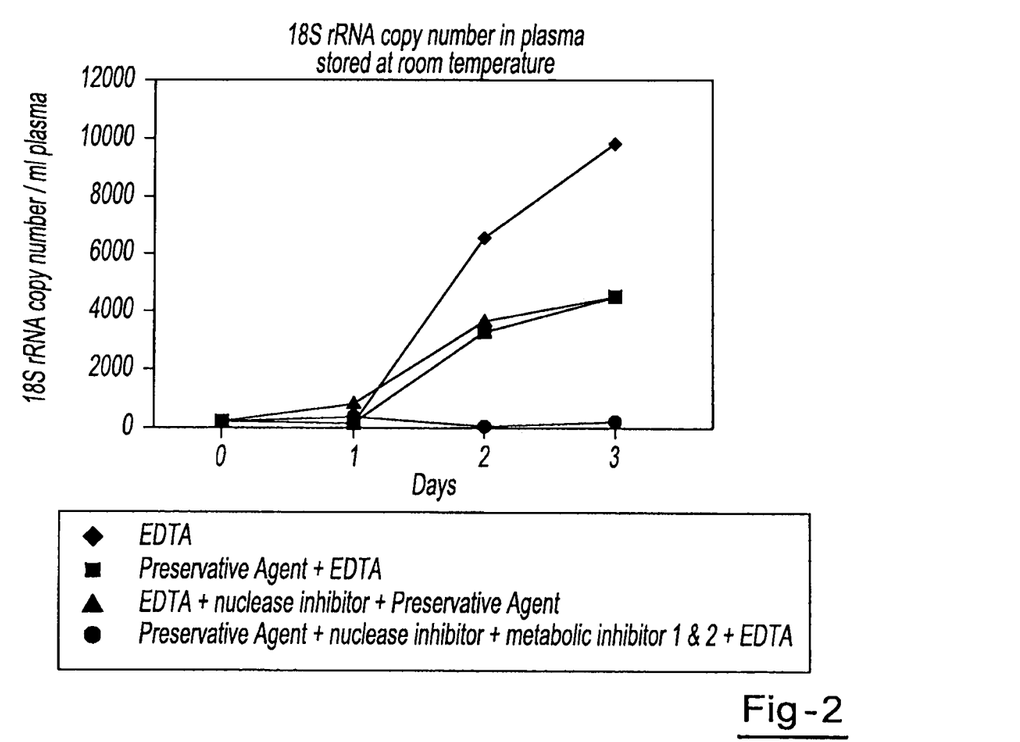
FIG. 2 is a graphic representation of showing the relative amounts of cell-free RNA present within four blood samples over time using the 18S rRNA copy number as a marker where an increase in the 18S rRNA copy number is indicative of cell lysis or increased cell metabolism; there is seen a plot of "preservative agent+nuclease inhibitor+metabolic inhibitor 1 & 2" that shows constant concentration of 18S rRNA that is indicative of uncontaminated (from cellular mRNA) and protected (from nuclease mediated degradation) cell-free mRNA.
Figure 3:
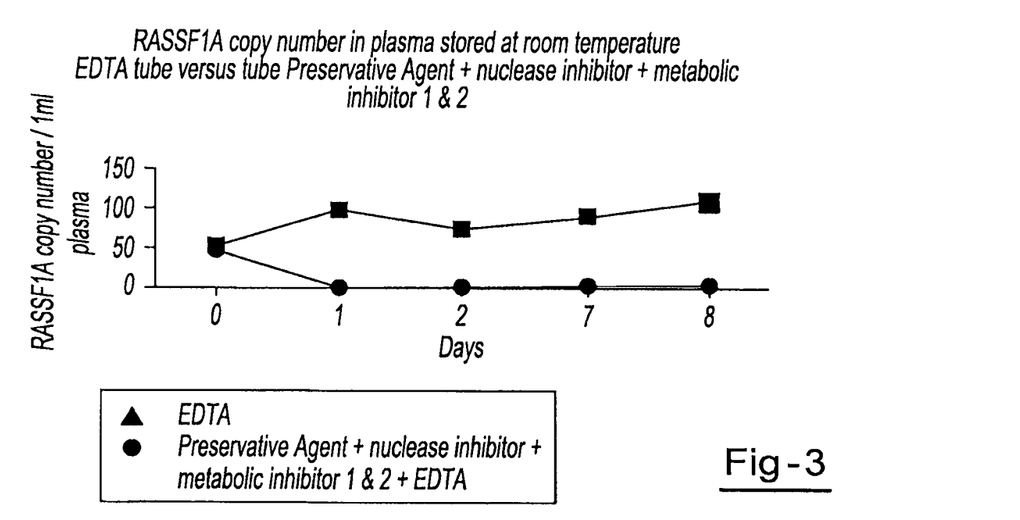
FIG. 3 is a graphic representation showing the relative amounts of cell-free RNA present within two blood samples over time using the RASSF1A copy number as a marker.

Examples 1, 2 and 3 above demonstrate an unexpected synergistic effect occurring only in blood samples contacted by a fixative, one or more enzyme inhibitors (e.g., nuclease inhibitors), and one or more metabolic inhibitors or more specifically, by a protective agent including DU, EDTA, ATA, glyceraldehyde and sodium fluoride. Blood samples contacted by only a fixative, only an enzyme inhibitor, only a metabolic inhibitor or any combination including less than all of the above components do not demonstrate the ability to maintain the integrity of the blood cells or the integrity of the nucleic acids. The combined effect of the DU, EDTA, ATA, glyceraldehydes and sodium fluoride far exceeds any expectations based on the effect, or lack thereof, of the DU, EDTA, ATA, glyceraldehydes or sodium fluoride used alone.

It will be appreciated that concentrates or dilutions of the amounts recited herein may be employed. In general, the relative proportions of the ingredients recited will remain the same. Thus, by way of example, if the teachings call for 30 parts by weight of a Component A, and 10 parts by weight of a Component B, the skilled artisan will recognize that such teachings also constitute a teaching of the use of Component A and Component B in a relative ratio of 3:1. Teachings of concentrations in the examples may be varied within about 25% (or higher) of the stated values and similar results are expected. Moreover, such compositions of the examples may be employed successfully in the present methods to isolate nucleic acids (e.g., cell-free RNA).

It will be appreciated that the above is by way of illustration only. Other ingredients may be employed in any of the compositions disclosed herein, as desired, to achieve the desired resulting characteristics. Examples of other ingredients that may be employed include antibiotics, anesthetics, antihistamines, preservatives, surfactants, antioxidants, unconjugated bile acids, mold inhibitors, nucleic acids, pH adjusters, osmolarity adjusters, or any combination thereof.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A composition for the stabilization of nucleic acids within a plasma sample comprising:
   a. an amount of free formaldehyde;
   b. about 200 to 500 g/L of one or more preservative agents including diazolidinyl urea;
   c. a solvent including water;
   wherein upon mixing the composition with a blood sample and storing the blood sample at room temperature for at least 7 days, cell-free RNA detection is improved due to reduced cellular RNA presence and a reduction in a decrease in cell-free RNA as a result of the composition.

2. The composition of claim 1, wherein the one or more preservative agents includes imidazolidinyl urea.

3. The composition of claim 1, further comprising one or more nuclease inhibitors that include an anticoagulant.

4. The composition of claim 2, further comprising one or more nuclease inhibitors that include an anticoagulant.

5. The composition of claim 3, wherein the one or more nuclease inhibitors includes EDTA.

6. The composition of claim 4, wherein the one or more nuclease inhibitors includes EDTA.

7. The composition of claim 1, wherein the one or more preservative agents includes imidazolidinyl urea, dimethyoylol-5,5dimethylhydantoin, dimethylol urea, 2-bromo-2-nitropropane-1,3-diol, oxazolidines, sodium hydroxymethyl glycinate, 5-hydroxymethoxymethyl-1-1aza-3,7-dioxabicyclo [3.3.0]octane, 5-hydroxymethyl-1-1aza-3,7dioxabicyclo[3.3.0]octane, quaternary adamantine and combinations thereof.

8. The composition of claim 5, wherein the one or more preservative agents includes imidazolidinyl urea, dimethoylol-5,5dimethylhydantoin, dimethylol urea, 2-bromo-2-nitropropane-1,3-diol, oxazolidines, sodium hydroxymethyl glycinate, 5-hydroxymethoxymethyl-1-1aza-3,7-dioxabicyclo [3.3.0]octane, 5-hydroxymethyl-1-1aza-3,7dioxabicyclo [3.3.0]octane, 5-hydroxypoly[methyleneoxy]methyl-1-1aza-3,7dioxabicyclo[3.3.0]octane, quaternary adamantine and any combination thereof.

9. The composition of claim 1, wherein the concentration of the one or more preservative agents is about 200 g/l to about 400 g/l.

10. The composition of claim 6, wherein the concentration of the one or more preservative agents is about 200 g/l to about 400 g/l.

11. The composition of claim 8, wherein the concentration of the one or more preservative agents is about 200 g/l to about 400 g/l.

12. The composition of claim 1, wherein the composition is mixed with a blood sample so that the amount of the one or more preservative agents is less than 10 g/l of the blood sample.

13. The composition of claim 2, wherein the composition is mixed with a blood sample so that the amount of the one or more preservative agents is less than 10 g/l of the blood sample.

14. The composition of claim 7, wherein the composition is mixed with a blood sample so that the amount of the one or more preservative agents is less than 10 g/l of the blood sample.

15. The composition of claim 1, wherein the composition is located into a tube having an interior wall that is flame sprayed, subjected to corona discharge, plasma treated, coated or otherwise treated.

16. The composition of claim 2, wherein the composition is located into a tube having an interior wall that is flame sprayed, subjected to corona discharge, plasma treated, coated or otherwise treated.

17. The composition of claim 7, wherein the composition is located into a tube having an interior wall that is flame sprayed, subjected to corona discharge, plasma treated, coated or otherwise treated.

18. The composition of claim 15, wherein the interior wall includes a coating that is sprayed, dipped, swabbed, or otherwise applied onto some or all of the interior wall of the tube.

19. The composition of claim 16, wherein the interior wall includes a coating that is sprayed, dipped, swabbed, or otherwise applied onto some or all of the interior wall of the tube.

20. The composition of claim 1, wherein the composition is located into a tube that is glass.

* * * * *